United States Patent
Kita et al.

(10) Patent No.: US 7,557,067 B2
(45) Date of Patent: Jul. 7, 2009

(54) PYRAZOLE SULFONYLUREA COMPOUND AND HERBICIDE

(75) Inventors: Hiroshi Kita, Funabashi (JP); Yoshitake Tamada, Funabashi (JP); Yoshihiko Nakaya, Funabashi (JP); Tetsuhiko Yano, Minamisaitama-gun (JP); Manabu Saeki, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 354 days.

(21) Appl. No.: 11/587,625

(22) PCT Filed: Apr. 27, 2005

(86) PCT No.: PCT/JP2005/008062

§ 371 (c)(1),
(2), (4) Date: Oct. 26, 2006

(87) PCT Pub. No.: WO2005/103044

PCT Pub. Date: Nov. 3, 2005

(65) Prior Publication Data

US 2008/0064600 A1    Mar. 13, 2008

(30) Foreign Application Priority Data

Apr. 27, 2004 (JP) ............... 2004-130933

(51) Int. Cl.
*C07D 413/14* (2006.01)
*A01N 43/88* (2006.01)

(52) U.S. Cl. ........................... 504/223; 544/65
(58) Field of Classification Search ............... 544/65; 504/223

See application file for complete search history.

(56) References Cited

U.S. PATENT DOCUMENTS 3,420,824 A    1/1969    Ellis
5,476,936 A *  12/1995   Philipp et al. ............ 504/223
5,847,126 A    12/1998   Philipp et al.

FOREIGN PATENT DOCUMENTS

JP    A 3-27368    2/1991
JP    A 7-118269   5/1995

OTHER PUBLICATIONS

STN printout for US Pat. No. 5,476,936 (total of pages).*

* cited by examiner

*Primary Examiner*—Kahsay T Habte
(74) *Attorney, Agent, or Firm*—Oliff & Berridge, PLC

(57) ABSTRACT

There is provided a novel herbicide. A pyrazole sulfonylurea compound of formula (1):

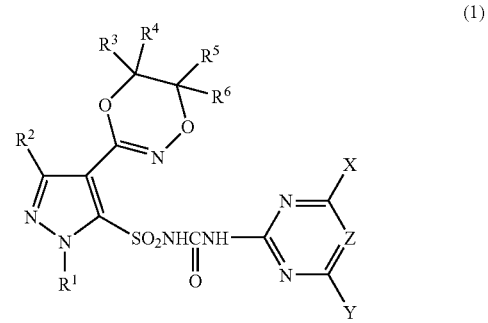

wherein $R^1$ is $C_{1-3}$alkyl, etc., $R^2$ is hydrogen atom, $C_{1-3}$alkyl, $C_{1-3}$haloalkyl, etc., $R^3$, $R^4$, $R^5$ and $R^6$ independently of one another are hydrogen atom, $C_{1-3}$alkyl, etc., with a proviso that at least one of $R^3$, $R^4$, $R^5$ and $R^6$ is $C_{1-3}$alkyl or $C_{1-3}$haloalkyl, X and Y independently of each other are $C_{1-3}$alkyl, etc., Z is nitrogen atom or methyne, and a salt thereof that is acceptable as an agrochemical; an agrochemical containing at least one of the compound and the salt thereof that is acceptable as an agrochemical as an active component, and a herbicide containing at least one of the compound and the salt thereof that is acceptable as an agrochemical as an active component.

7 Claims, No Drawings

PYRAZOLE SULFONYLUREA COMPOUND AND HERBICIDE

TECHNICAL FIELD

The present invention relates to pyrazole sulfonylurea compounds and agrochemicals containing them as active components, particularly as herbicides.

BACKGROUND ART

It is disclosed in Patent Document 1 that pyrazole sulfonylureas that a dioxadine ring is bonded on the pyrazole ring have herbicidal activity. However, Patent document 1 does not concretely disclose pyrazole sulfonylureas that any substituents are bonded on the dioxadine ring on the pyrazole ring.

Patent Document 1: JP-A-7-118269 (1995)

DISCLOSURE OF INVENTION

Problem to be Solved by Invention

An object of the present invention is to provide agrochemicals, particularly herbicides, containing pyrazole sulfonylurea compounds as active components and having excellent efficacy.

Means for Solving Problem

The present inventors eagerly investigated for solving the above-mentioned problems, as a result of it, they found that novel pyrazole sulfonylurea compounds have a herbicidal activity and a selective action for crops, and completed the present invention.

That is, the present invention relates to a pyrazole sulfonylurea compound (hereinafter referred to as "compound of the present invention") of formula (1):

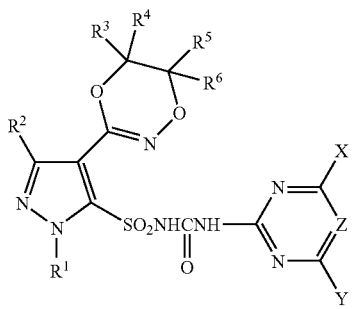

(1)

wherein $R^1$ is $C_{1-3}$alkyl, $C_{1-3}$haloalkyl, $C_{1-3}$alkoxy $C_{1-3}$alkyl, phenyl or pyridyl, $R^2$ is hydrogen atom, $C_{1-3}$alkyl, $C_{1-3}$haloalkyl, $C_{1-3}$alkoxy or halogen atom, $R^3$, $R^4$, $R^5$ and $R^6$ independently of one another are hydrogen atom, $C_{1-3}$alkyl or $C_{1-3}$haloalkyl, with a proviso that at least one of $R^3$, $R^4$, $R^5$ and $R^6$ is $C_{1-3}$alkyl or $C_{1-3}$haloalkyl, X and Y Independently of each other are $C_{1-3}$alkyl, $C_{1-3}$haloalkyl, $C_{1-3}$alkoxy; $C_{1-3}$haloalkoxy, halogen atom or di($C_{1-3}$alkyl)amino, Z is nitrogen atom or methyne, and a salt thereof that is acceptable as an agrochemical;

an agrochemical containing at least one of the compound of the present invention and the salt thereof that is acceptable as an agrochemical as an active component, and a herbicide containing at least one of the compound of the present invention and the salt thereof that is acceptable as an agrochemical as an active component.

Further, the compound of the present invention and the salt thereof that is acceptable as an agrochemical are used in a mixed formulation with some sort of herbicide and exert a synergetic herbicidal effect with the herbicide.

Effect of Invention

The pyrazole sulfonylurea compound of the present invention has an excellent herbicidal effect against weeds and at the same time shows no crop injury on rice and wheat or barley, and thus it is an excellent selective herbicidal compound for paddy rice and wheat or barley.

BEST MODE FOR CARRYING OUT THE INVENTION

The substituents $R^1$, $R^2$, $R^3$, $R^4$, $R^5$, $R^6$, X, Y and Z in the compound of the present invention and the production intermediate of the compound of the present invention are exemplified. In the meantime, symbols have the following meanings: Me is methyl, Et is ethyl, Pr-n is n-propyl, Pr-iso is isopropyl, Ph is phenyl, and Py is pyridyl.

Concrete Examples of Substituent $R^1$

Me, Et, Pr-n, Pr-iso, $CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2CH_2Cl$, $CH_2CH_2Br$, $CH_2OMe$, $CH_2OEt$, $CH_2OPr-n$, $CH_2OPr-iso$, $CH_2CH_2OMe$, $CH_2CH_2OEt$, $CH_2CH_2OPr-n$, $CH_2CH_2OPr-iso$, $CH_2CH_2$ $CH_2OMe$, $CH_2CH_2$ $CH_2OEt$, $CHMeCH_2OMe$, $CH_2CHMeOMe$, Ph, 2-Py.

Concrete Examples of Substituent $R^2$

H, Me, Et, Pr-n, Pr-iso, $CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2CH_2Cl$, OMe, OEt, OPr-n, OPr-iso, F, Cl, Br, I.

Concrete Examples of Substituents $R^3$, $R^4$, $R^5$ and $R^6$

H, Me, Et, Pr-n, Pr-iso, $CH_2F$, $CHF_2$, $CF_3$, $CH_2Cl$, $CHCl_2$, $CCl_3$, $CH_2Br$, $CH_2I$, $CH_2CH_2F$, $CH_2CHF_2$, $CH_2CF_3$, $CH_2CH_2CH_2F$.

Concrete Examples of Substituents X and Y

Me, Et, Pr-n, Pr-iso, $OCH_3$, $OCH_2CH_3$, OPr-n, OPr-iso, $CH_2F$, $CHF_2$, $CF_3$, $CH_2Cl$, CHCl, $CCl_3$, $CH_2CH_2F$, $CH_2CHF_2$, $CH_2CF_3$, $CF_2CF_3$, $CH_2CH_2CH_2F$, $CH_2CH_2CHF_2$, $CH_2CH_2CF_3$, $CH_2CH_2Cl$, $CH_2CH_2Br$, $OCH_2F$, $OCHF_2$, $OCF_3$, $OCH_2CH_2F$, $OCH_2CHF_2$, $OCH_2CF_3$, $OCF_2CF_3$ $OCH_2CH_2CH_2F$, $OCH_2CH_2CHF_2$, $OCH_2CH_2CF_3$, $OCH_2CH_2Cl$, $OCH_2CH_2Br$, F, Cl, Br, I, $Me_2N$, $Et_2N$, $(Pr-n)_2N$.

Concrete Examples of Substituent Z

N, CH.

Some of the compounds (1) according to the present invention have optical isomers, and all of the optical isomers are included in the present invention.

In the meantime, among the compounds of the present invention, for example, in which $R^2$ is Cl have a low crop injury on rice transplanted at a depth of 0 cm, and they tend to have a low crop injury particularly under water leakage condition near to practical scene also on transplanted rice.

The compound (1) of the present invention can be produced according to methods shown in reaction formulae 1 to 3 described below.

[Reaction formula 1]

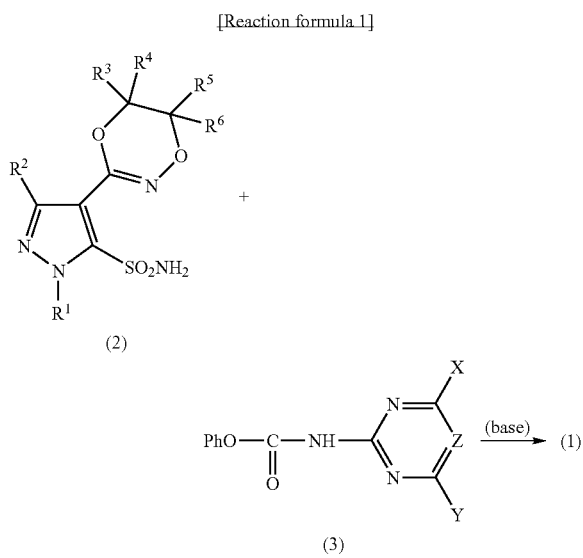

wherein $R^1$, $R^2$, $R^3$, $R^4$, $R^5$, $R^6$, X, Y and Z are as defined above.

Reaction equation 1 shows the production of the compound (1) of the present invention by reacting 4-(5H,6H-1,4,2-dioxadin-3-yl)pyrazole-5-sulfonamide (2) with 2-phenoxycarbonyl aminopyrimidine (or triazine) (3) in the presence or absence of a base.

In this reaction, (3) is generally used in a molar amount of 0.5 to 10-fold, preferably 0.9 to 1.1-fold over (2).

The base used in this reaction includes inorganic bases such as sodium hydroxide, potassium hydroxide, potassium carbonate, sodium carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (2).

This reaction proceeds even without solvent, but a Solvent can be used if necessary. The solvent is not specifically limited so long as it is inactive in this reaction, and Includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., and mixed solvents thereof.

The reaction temperature is generally −90 to 200° C., preferably 0 to 120° C.

The reaction time is generally 0.05 to 100 hour, preferably 0.5 to 10 hours.

[Reaction formula 2]

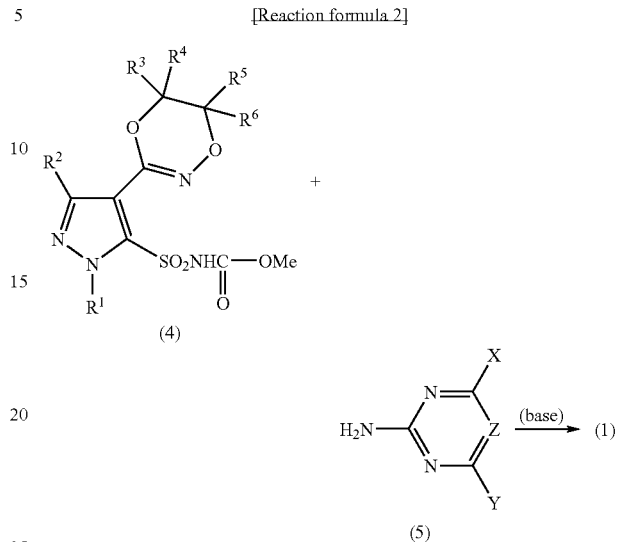

wherein $R^1$, $R^2$, $R^3$, $R^4$, $R^5$, $R^6$, X, Y and Z are as defined above.

Reaction equation 2 shows the production of the compound (1) of the present invention by reacting 4-(5H,6H-1,4,2-dioxadin-3-yl)pyrazole-5-sulfonylcarbamate (4) with 2-aminopyrimidine (or triazine) (5) in the presence or absence of a base. In this reaction, (5) is generally used in a molar amount of 0.5 to 10-fold, preferably 0.9 to 1.1-fold over (4).

The base used in this reaction includes inorganic bases such as sodium hydroxide, potassium hydroxide, potassium carbonate, sodium carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (4).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., and mixed solvents thereof.

The reaction temperature is generally −90 to 200° C., preferably 0 to 120° C.

The reaction time is generally 0.05 to 100 hours, preferably 0.5 to 10 hours.

[Reaction formula 3]

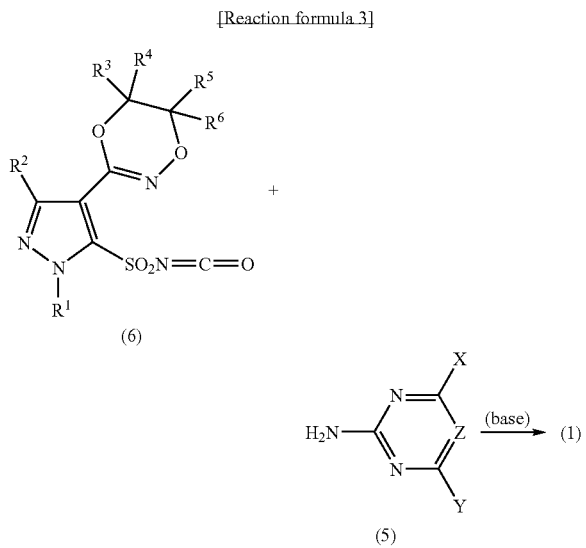

wherein $R^1$, $R^2$, $R^3$, $R^4$, $R^5$, $R^6$, X, Y and Z are as defined above.

Reaction equation 3 shows the production of the compound (1) of the present invention by reacting 4-(5H,6H-1,4,2-dioxadin-3-yl)pyrazole-5-sulfonylisocyanate (6) with 2-aminopyrimidine (or triazine) (5) in the presence or absence of a base. In this reaction, (5) is generally used in a molar amount of 0.5 to 10-fold, preferably 0.9 to 1.1-fold over (6).

The base used in this reaction includes Inorganic bases such as sodium hydroxide, potassium hydroxide, potassium carbonate, sodium carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (6).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., and mixed solvents thereof.

The reaction temperature is generally −90 to 200° C., preferably 0 to 120° C.

The reaction time is generally 0.05 to 100 hours, preferably 0.5 to 10 hours.

4-(5H,6H-1,4,2-dioxadin-3-yl)pyrazole-5-sulfonamide (2) used in Reaction formula 1 can be produced according to the methods shown in Reaction formulae 4 to 6.

In addition, 4-(5H,6H-1,4,2-dioxadin-3-yl)pyrazole-5-sulfonyl carbamate (4) and 4-(5H,6H-1,4,2-dioxadin-3-yl)pyrazole-5-sulfonyl isocyanate (6) used in Reaction formulae 2 and 3 can be synthesized by using 4-(5H,6H-1,4,2-dioxadin-3-yl)pyrazole-5-sulfonamide (2) as a starting material by reference to the methods disclosed in JP-A-59-219281 (1984) and JP-A-55-13266 (1980).

[Reaction formula 4]

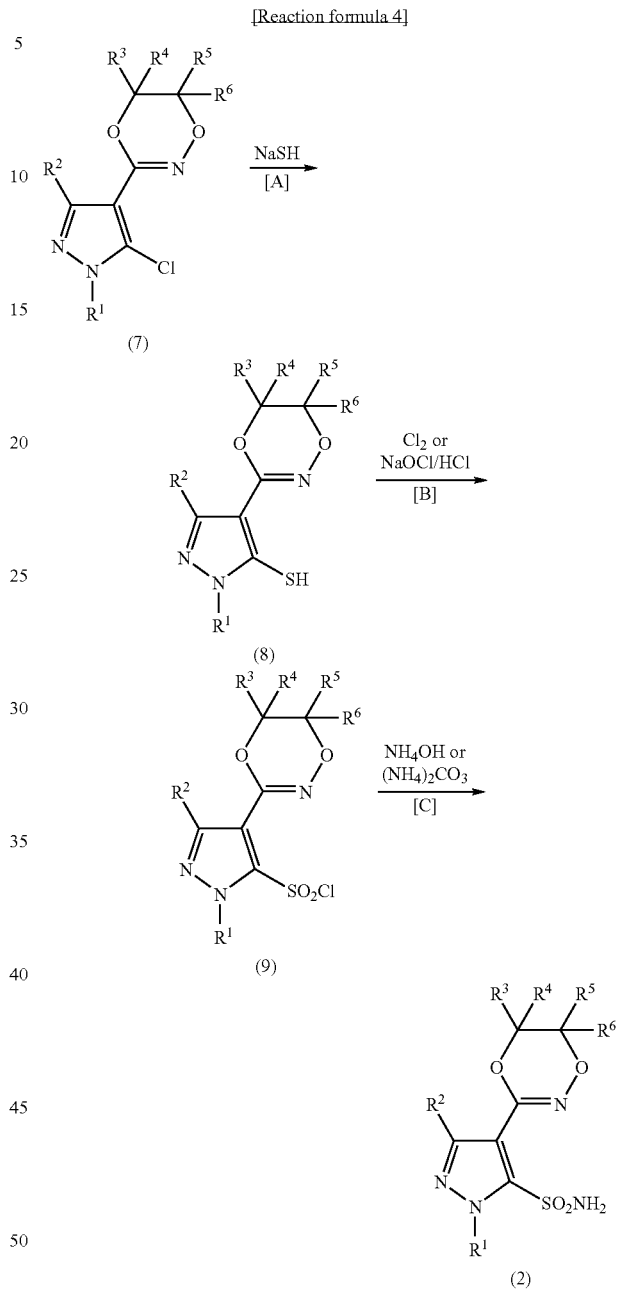

wherein $R^1$, $R^2$, $R^3$, $R^4$, $R^5$ and $R^6$ are as defined above.

Reaction equation 4 shows the production of 4-(5H,6H-1,4,2-dioxadin-3-yl)pyrazole-5-sulfonamide (2) by reacting 5-chloro-4-(5H,6H-1,4,2-dioxadin-3-yl)pyrazole (7) with sodium hydrosulfide to obtain 5-mercapto-4-(5H,6H-1,4,2-dioxadin-3-yl)pyrazole (8) (step A), then reacting (8) with a chlorinating agent such as chlorine or sodium hypochlorite to obtain 4-(5H,6H-1,4,2-dioxadin-3-yl)pyrazole-5-sulfonyl chloride (9) (step B), and reacting (9) with ammonia water or ammonium carbonate (step C).

In step A, sodium hydrosulfide is generally used in a molar amount of 1.0 to 10-fold, preferably 2 to 5-fold over (7).

This reaction proceeds even without solvent, but a solvent can be used if necessary.

The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., sulfur-containing polar solvents such as dimethylsulfoxide and sulfolane, etc., water, and mixed solvents thereof.

The reaction temperature is generally −90 to 200° C., preferably 0 to 120° C.

The reaction time is generally 0.05 to 100 hours, preferably 0.5 to 10 hours.

In step B, chlorine or sodium hypochlorite is generally used in a molar amount of 1 to 100-fold, preferably 2 to 10-fold over (8).

In this reaction, a solvent can be used if necessary. The solvent is not specifically limited so long as it is inactive in this reaction, and includes for example halogen-containing hydrocarbons such as carbon tetrachloride, chloroform and 1,2-dichloroethane, etc., water, and mixed solvents thereof.

The reaction temperature is generally −90 to 100° C., preferably −10 to 50° C.

The reaction time is generally 0.05 to 100 hours, preferably 0.5 to 10 hours.

In step C, ammonia or ammonium carbonate is generally used in a molar amount of 1.0 to 10-fold, preferably 2 to 5-fold over (9).

This reaction proceeds even without solvent but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., sulfur-containing polar solvents such as dimethylsulfoxide and sulfolane, etc., water, and mixed solvents thereof.

The reaction temperature is generally −90 to 200° C., preferably 0 to 100° C.

The reaction time is generally 0.05 to 100 hours, preferably 0.5 to 10 hours.

[Reaction formula 5]

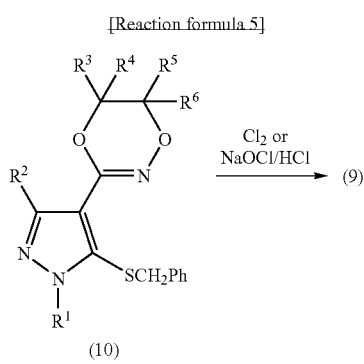

wherein $R^1$, $R^2$, $R^3$, $R^4$, $R^5$ and $R^6$ are as defined above.

Reaction equation 5 shows the production of 4-(5H,6H-1,4,2-dioxadin-3-yl)pyrazole-5-sulfonyl chloride (9) by reacting 5-benzylmercapto-4-(5H,6H-1,4,2-dioxadin-3-yl)pyrazole (10) with a chlorinating agent such as chlorine or sodium hypochlorite. In this reaction, chlorine or sodium hypochlorite is generally used in a molar amount of 1 to 100-fold, preferably 2 to 1-fold over (10).

In this reaction, a solvent can be used if necessary. The solvent is not specifically limited so long as it is inactive in this reaction, and includes for example halogen-containing hydrocarbons such as carbon tetrachloride, chloroform and 1,2-dichloroethane, etc., water, and mixed solvents thereof.

The reaction temperature is generally −90 to 100° C., preferably −50 to 50° C.

The reaction time is generally 0.05 to 100 hours, preferably 0.5 to 10 hours.

(9) can be derived into 4-(5H,6H-1,4,2-dioxadin-3-yl)pyrazole-5-sulfonamide (2) according to step C of Reaction formula 4.

[Reaction formula 6]

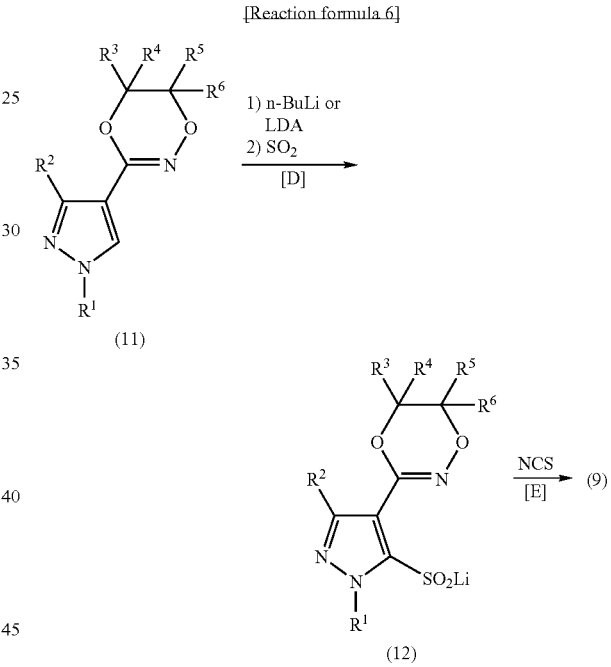

wherein $R^1$, $R^2$, $R^3$. $R^4$. $R^5$ and $R^6$ are as defined above.

Reaction equation 6 shows the production of 4-(5H,6H-1,4,2-dioxadin-3-yl)pyrazole-5-sulfonylchloride (9) by subjecting 5-position on the pyrazole ring of 4-(5H,6H-1,4,2-dioxadin-3-yl)pyrazole (11) to lithiation with lithium n-butyl or lithium diidopropylamide, etc., then reacting with sulfur dioxide to obtain 4-(5H,6H-1,4,2-dioxadin-3-yl)pyrazole-5-sulfonic acid lithium (12) (step D), and reacting (12) with N-chlorosuccinimide (step E).

In reaction 1) of step D, lithium n-butyl or lithium diidopropylamide is generally used in a molar amount of 1 to 100-fold, preferably 1 to 5-fold over (11).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., ethers such as diethyl ether, diisopropyl ether, dioxane and tetrahydrofuran, etc., and mixed solvents thereof.

The reaction temperature is generally −120 to 100° C., preferably −78 to 10° C.

The reaction time is generally 0.05 to 100 hours, preferably 0.5 to 10 hours.

In reaction 2) of step D, sulfur dioxide is generally used in a molar amount of 1.0 to 100-fold, preferably 1 to 10-fold over (11).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., ethers such as diethyl ether, diisopropyl ether, dioxane and tetrahydrofuran, etc., and mixed solvents thereof.

The reaction temperature is generally −120 to 100° C., preferably −78 to 10° C.

The reaction time is generally 0.05 to 100 hours, preferably 0.5 to 10 hours.

In step E, N-chlorosuccinimide is generally used in a molar amount of 1.0 to 100-fold, preferably 1 to 10-fold over (11).

The solvent is not specifically limited so long as it is inactive in this reaction, and includes for example halogen-containing hydrocarbons such as carbon tetrachloride, chloroform and 1,2-dichloroethane, etc., water, and mixed solvents thereof.

The reaction temperature is generally −90 to 100° C., preferably −10 to 50° C.

The reaction time is generally 0.05 to 100 hours, preferably 0.5 to 10 hours.

(9) can be derived into 4-(5H,6H-1,4,2-dioxadin-3-yl)pyrazole-sulfonamide (2) according to step C of Reaction formula 4.

5-Chloro-4-(5H,6H-1,4,2-dioxadin-3-yl)pyrazole (7), 5-benzylmercapto-4-(4H,6H-1,4,2-dioxadin-3-yl)pyrazole (10) and 4-(4H,6H-1,4,2-dioxadin-3-yl)pyrazole (11) used in the methods shown in Reaction formulae 4 to 6 can be produced by methods shown in Reaction formulae 7 to 15.

wherein $R^1$, $R^2$, $R^5$, $R^4$, $R^5$ and $R^6$ are as defined above, $X^1$ is halogen atom and L is chlorine atom, benzylthio or hydrogen atom.

Reaction equation 7 shows the production of 4-(5H,6H-1,4,2-dioxadin-3-yl)pyrazole (7), (10) or (11) by reacting pyrazole-4-hydroxamic acid (13) with an adjacently dihalogenated alkyl (14).

In this reaction, (14) is generally used in a molar amount of 1.0 to 100-fold, preferably 1 to 5-fold over (13).

The base used in this reaction includes Inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (13).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitrites such as acetonitrile and propionitrile, etc., amides such as N,N-dimethylformamide, N,N-dimethylacetamide and N-methyl-2-pyrrolidone, etc., sulfur-containing polar solvents such as dimethylsulfoxide and sulfolane, etc., water, and mixed solvents thereof.

The reaction temperature is generally −90 to 200° C., preferably 0 to 100° C.

The reaction time is generally 0.05 to 100 hours, preferably 0.5 to 10 hours.

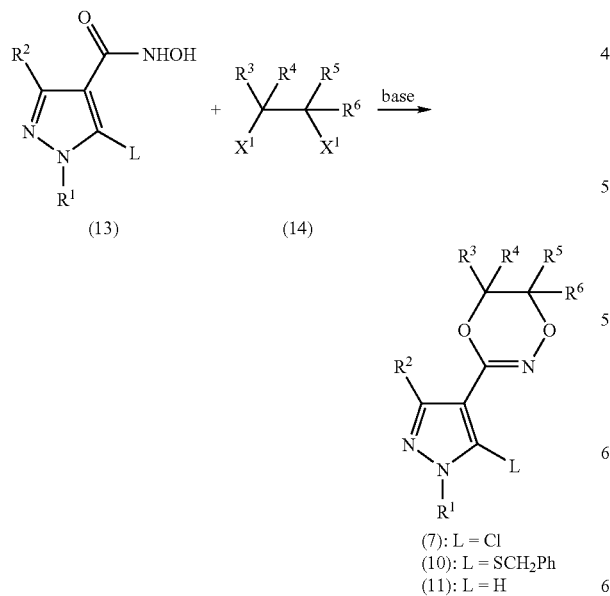

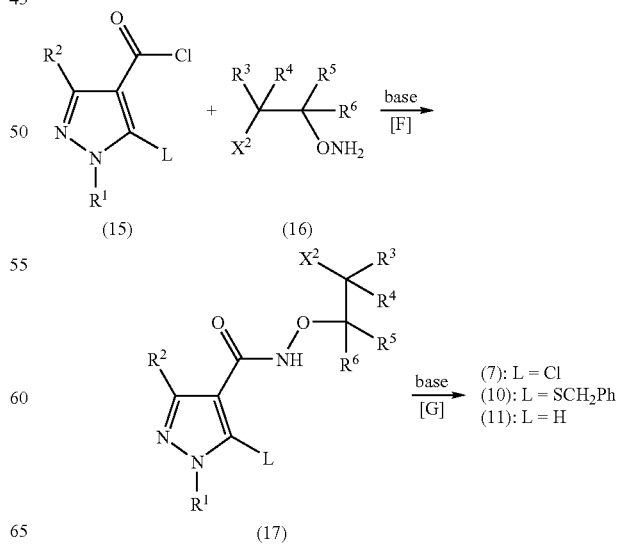

wherein $R^1$, $R^2$, $R^3$, $R^4$, $R^5$, $R^6$ and L are as defined above, and $X^2$ is halogen atom, $C_{1-3}$alkylsulfonyloxy or $C_{1-3}$haloalkylsulfonyloxy].

Reaction equation 8 shows the production of 4-(5H,6H-1,4,2-dioxadin-3-yl)pyrazole (7), (10) or (11) by reacting pyrazole-4-carboxylic acid chloride (15) with an alkoxyamine (16) to obtain pyrazole-4-hydroxamic acid ester (17) (step F), and reacting (17) with a base (step G).

In the reaction of step F, (16) is generally used in a molar amount of 1 to 100-fold, preferably 2 to 5-fold over (15).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (15).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

The base used in the reaction of step G includes inorganic bases such as sodium hydroxide, potassium hydroxide, potassium carbonate, sodium carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 2-fold over (17).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

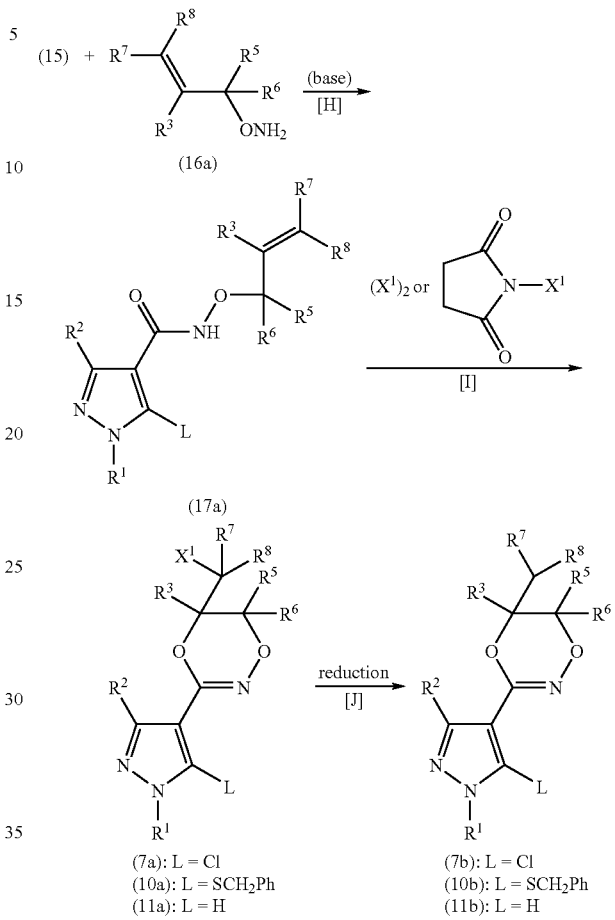

[Reaction formula 9]

wherein $R^1$, $R^2$, $R^3$, $R^5$, $R^6$, $X^1$ and L are as defined above, and $R^7$ and $R^8$ independently of each other are halogen atom or $C_{1-3}$alkyl].

Reaction equation 9 shows the production of 4-(5-alkyl-5H,6H-1,4,2-dioxadin-3-yl)pyrazole (7b), (10b) or (11b) by reacting pyrazole-4-carboxylic acid chloride (15) with allyloxyamine (16a) to obtain pyrazole-4-hydroxamic acid ester (17a) (step H), reacting (17a) with a halogen or N-halogenated succinimide to obtain 4-(5-haloalkyl-5H,6H-1,4,2-dioxadin-3-ylpyrazole (7a), (10a) or (11a) (step I), and reducing (7a), (10a) or (11a) (step J).

In the reaction of step H, (16a) is generally used in a molar amount of 1 to 100-fold, preferably 2 to 5-fold over (15).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The bass is generally used in a molar amount of 0 to 10-fold, preferably 0 to 2-fold over (15).

This reaction proceeds even without solvent, but a solvent can b used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

In the reaction of step I, the halogen or N-halogeno succinimide is generally used in a molar amount of 1 to 100-fold, preferably 1 to 5-fold over (17a).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketone such as acetone, methyl ethyl ketone and methylisobutyl ketone, etc., nitriles such as acetonitrile and propionitrile, etc., carbonic acid esters such as met acetate or ethyl acetate, etc., alcohols such as methanol, ethanol or ethylene glycol, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

The reducing agents and reducing systems used in the reaction of stop J include a system in which an alkali metal is used, such as metal sodium/liquid ammonia, metal lithium/liquid ammonia and metal sodium/t-butyl alcohol-tetrahydrofuran mixed solvent, etc., a system in which metal zinc is used, such as zinc/acetic acid and zinc/potassium hydroxide/water, etc., a system in which an organic tin hydride is used, such as triphenyl tin hydride, diphenyl tin hydride, tri n-butyl tin hydride, di n-butyl tin hydride, triethyl tin hydride and trimethyl tin hydride, etc., a mixed system in which the above-mentioned organic tin compound is combined with a free radical initiator such as azobisisobutyronitrile, etc., a system in which silanes such as trichlorosilane, triethylsilane and trimethylsilane, etc. are used, a system in which a metal hydrogen complex compound such as aluminum lithium hydride, aluminum sodium hydride, bis(2-methoxyethoxy) aluminum sodium hydride, sodium boron hydride and cyano boron sodium hydride, etc. is used, a system in which a borane derivative such as diborane, trimethylamine-borane and pyridine-borane, etc. is used, and a catalytic reduction system such as hydrogen/palladium-carbon and hydrogen/Raney nickel, etc.

The reducing agent is generally used in a molar amount of 1 to 100-fold, preferably 1 to 5-fold over (7a), (10a) or (11a).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitrites such as acetonitrile and propionitrile, etc., carbonic acid esters such as methyl acetate or ethyl acetate, etc., alcohols such as methanol, ethanol or ethylene glycol, etc., amides such as N,N-dimethylformamide, N,N-dimethylacetamide and N-methyl-2-pyrrolidone, etc., water, and mixed solvents thereof.

The reaction temperature is generally −90 to 200° C., preferably −78 to 100° C.

The reaction time is generally 0.05 to 100 hours, preferably 0.5 to 10 hours.

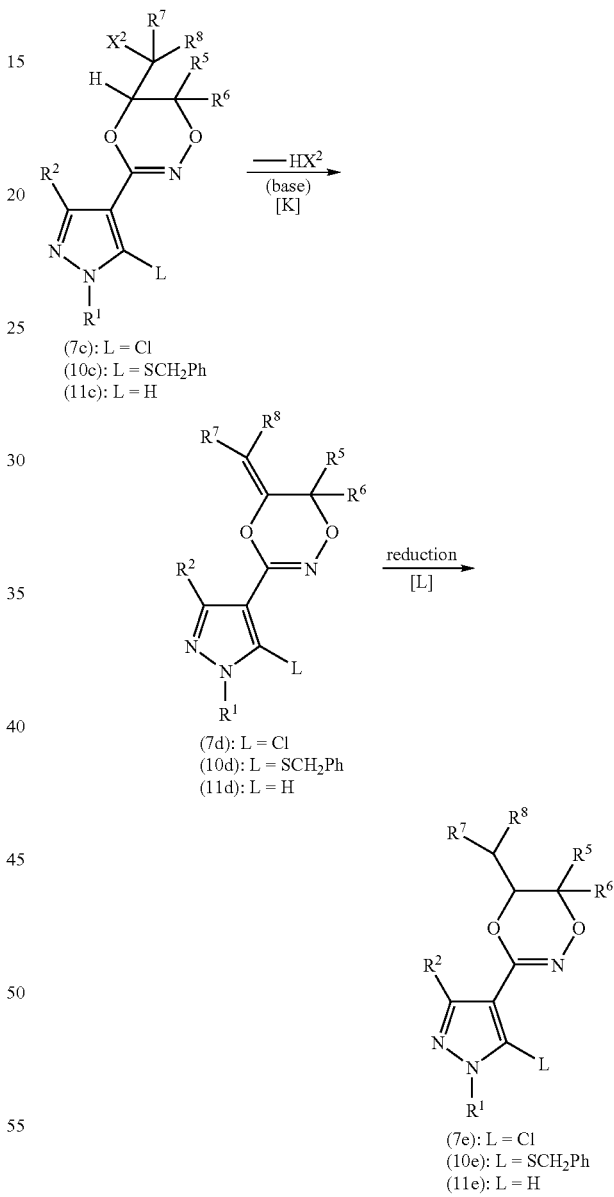

wherein $R^1$, $R^2$, $R^5$, $R^6$, $R^7$, $R^8$, $X^2$ and L are as defined above.

Reaction equation 10 shows the production of each 4-(5-alkyl-5H,6H-1,4,2-dioxadin-3-yl)pyrazole (7e), (10e) or (11e) by subjecting 4-(5-haloalkyl-5H,6H-1,4,2-dioxadin-3-yl)pyrazole (7c), (10c) or (11c) to dehydrohalogenation in the presence or absence of a base to obtain each 4-(5-alkylidene-5H,6H-1,4,2-dioxadin-3-yl)pyrazole (7d), (10d) or (11d) (step K), reducing (7d), (10d) or (11d) (step L).

The base used in the reaction of step K includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo [5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 100-fold, preferably 0 to 5-fold over (7c), (10c) or (11c).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

The reducing agents and reducing systems used in the reaction of step L include a system in which an alkali metal is used, such as metal sodium/liquid ammonia, metal lithium/liquid ammonia and metal lithium/ethyl amine, etc., a system in which metal aluminum is used, such as aluminum-mercury/diethylether-water and aluminum-nickel/sodium hydroxide/water, etc., a system in which an aluminum hydride compound such as diisobutyl aluminum hydride, etc. is used, a system in which hydrosilanes such as triethylsilane-trifluoroacetic acid and polymethylhydrosiloxane/palladium-carbon, etc. are used, a system in which a metal hydrogen complex compound such as aluminum lithium hydride, aluminum sodium hydride, bis(2-methoxyethoxy) aluminum sodium hydride, sodium boron hydride and cyano boron sodium hydride, etc. is used, a system in which a borane derivative such as diborane, trimethylamine-borane and pyridine-borane, etc. is used, a system in which a di-imide generated in the reaction system is used, such as hydrazine hydrate/air, hydrazine hydrate/hexacyano iron (III) acid potassium and hydroxyamine-O-sulfonic acid/sodium hydroxide, etc., a heterogeneous catalytic reduction system such as hydrogen/palladium-carbon and hydrogen/Raney nickel, etc., and homogeneous catalytic reduction system such as hydrogen/chlorotris(triphenylphosphine)rhodium (I), hydrogen/hydride carbonyltris(triphenylphosphino) rhodium (I), hydrogen/rhodium (II) acetate and hydrogen/ruthenium (II) acetate, etc.

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., carbonic acid esters such as methyl acetate or ethyl acetate, etc., alcohols such as methanol, ethanol or ethylene glycol, etc., amides such as N,N-dimethylformamide, N,N-dimethylacetamide and N-methyl-2-pyrrolidone, etc. water, and mixed solvents thereof.

The reaction temperature is generally −90 to 200° C., preferably −78 to 100° C.

The reaction time is generally 0.05 to 100 hours, preferably 0.5 to 10 hours.

[Reaction formula 11]

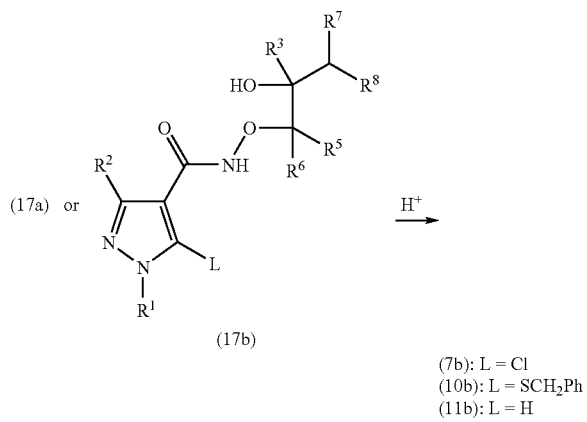

(7b): L = Cl
(10b): L = SCH$_2$Ph
(11b): L = H wherein $R^1$, $R^2$, $R^3$, $R^5$, $R^6$, $R^7$, $R^8$ and L are as defined above.

Reaction equation 11 shows the production of 4-(5-alkyl-5H,6H-1,4,2-dioxadin-3-yl)pyrazole (7b), (10b) or (11b) by reacting pyrazole-4-hydroxamic acid ester (17a) or (17b) with an acid.

The acid used in this reaction includes inorganic acids such as hydrochloric acid, sulfuric acid and phosphoric acid, etc., organic acids such as acetic acid, trifluoroacetic acid, methane sulfonic acid, trifluoromethane sulfonic acid or p-toluenesulfonic acid, etc.

The acid is generally used in a molar amount of 0.01 to 100-fold, preferably 0.05 to 10-fold over (17a) or (17a).

This reaction proceeds even without solvent, but a solvent can be used if necessary. The solvent is not specifically limited so long as it is inactive in this reaction, and Includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

[Reaction formula 12]

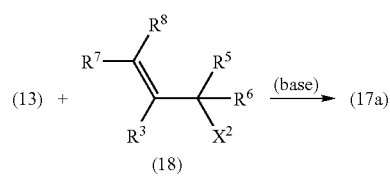

wherein $R^3$, $R^5$, $R^6$, $R^7$, $R^8$ and $X^2$ are as defined above.

Reaction equation 12 shows the production of pyrazole-4-hydroxamic acid ester (17a) by reacting pyrazole-4-hydroxamic acid (13) with halogenated allyl (18) in the presence or absence of a base.

In this reaction, (8) is generally used in a molar amount of 1- to 100-fold, preferably 1- to 5-fold over (13).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 100-fold, preferably 0 to 5-fold over (13).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

[Reaction formula 13]

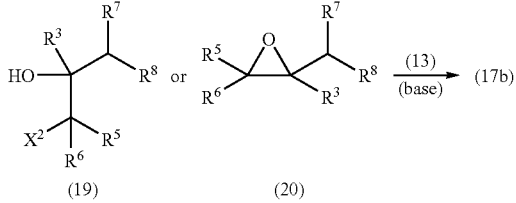

wherein $R^3$, $R^5$, $R^6$, $R^7$, $R^8$ and $X^2$ are as defined above.

Reaction equation 13 shows the production of pyrazole-4-hydroxamic acid ester (17b) used in Reaction formula 11 by reacting pyrazole-4-hydroxamic acid (13) with halohydrin (19) or oxyrane (20) in the presence or absence of a base.

In this reaction, (19) or (20) is generally used in a molar amount of 1 to 100 fold, preferably 2 to 5-fold over (13).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 100-fold, preferably 0 to 5-fold over (13).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

[Reaction formula 14]

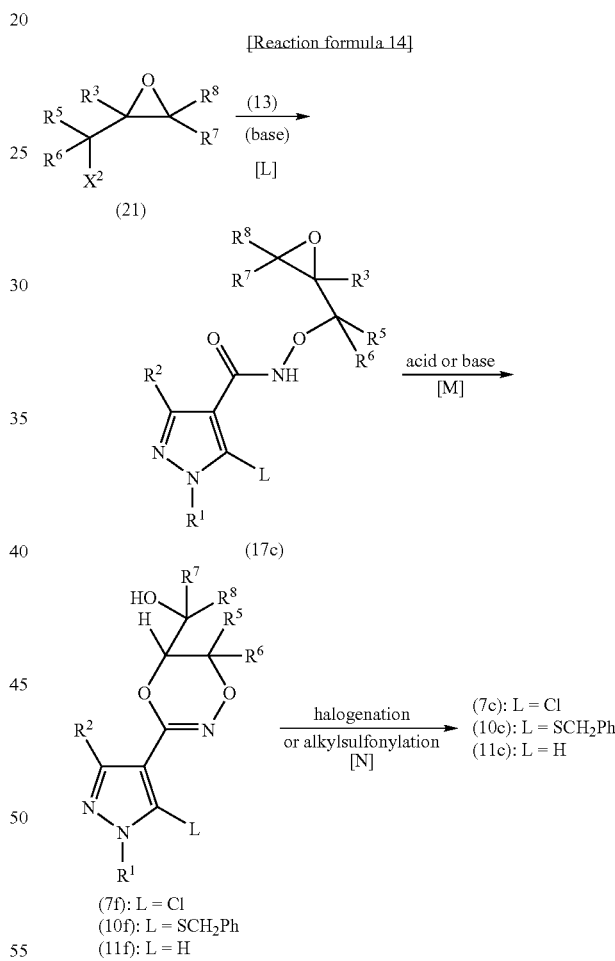

wherein $R^1$, $R^2$, $R^3$, $R^5$, $R^6$, $R^7$, $R^8$ and L are as defined above.

Reaction equation 14 shows the production of each 4-(5-haloalkyl (or alkylsulfonyloxyalkyl)-5H,6H-1,4,2-dioxadin-3-yl)pyrazole (7c), (10c) or (11c) by reacting pyrazole-4-hydroxamic acid (13) with epihalohydrin (21) in the presence or absence of a base to obtain pyrazole-4-hydroxamic acid ester (17c) (step L), treating (17c) with an acid or a base to obtain 4-(5-hydroxyalkyl-5H,6H-1,4,2-dioxadin-3-yl)pyrazole (7f), (10f) or (11f) (step M), and then subjecting (7f), (10f) or (11f) to halogenation or alkylsulfonylation (step N).

In the reaction of step L, (21) is generally used in a molar amount of 1 to 100-fold, preferably 1 to 5-fold over (13).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 10-fold, preferably 0 to 5-fold over (13).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., others such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., amides such as N,N-dimethylformamide, N,N-dimethylacetamide and N-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

The acid or base used in the reaction of step M includes inorganic acids such as hydrochloric acid, sulfuric acid and phosphoric acid, etc., organic acids such as acetic acid, trifluoroacetic acid, methane sulfonic acid, trifluoromethane sulfonic acid or p-toluenesulfonic acid, etc., inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The acid or bass is generally used in a molar amount of 0 to 100-fold, preferably 0 to 5-fold over (17c).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., carbonic acid esters such as methyl acetate or ethyl acetate, etc., alcohols such as methanol, ethanol or ethylene glycol, etc., amides such as N,N-dimethylformamide, N,N-dimethylacetamide and N-methyl-2-pyrrolidone, etc., water, and mixed solvents thereof.

The reaction temperature is generally −90 to 200° C., preferably −78 to 100° C.

The reaction time is generally 0.05 to 100 hours, preferably 0.5 to 10 hours.

In the reaction of step N, the halogenation agent or the alkylsulfonylation agent is generally used in a molar amount of 1 to 100-fold, preferably 1 to 5-fold over (7f), (10f) or (11f).

The halogenation agent used in this reaction includes hydrogen halogenic acids such as hydrogen chloride, hydrogen bromide and hydrogen iodide, etc., halogenated phosphorus such as phosphorus trichloride, phosphorus pentachloride, oxyphosphorus chloride and phosphorus tribromide, etc., a system such as triphenyl phosphonate/benzyl chloride and triphenylphosphine/carbon tetrachloride, etc., halogenated sulfonium such as methane sulfonyl chloride and p-toluene sulfonyl chloride, etc., and halogenated thionyl such as thionyl chloride and thionyl bromide, etc.

The alkylsulfonylation agent used in this reaction includes halogenated sulfonium such as methane sulfonyl chloride and p-toluene sulfonyl chloride, etc.

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl ether, diisopropyl ether, dioxane and tetrahydrofuran, etc., ketones such as acetone, methyl ethyl ketone and methylisobutyl ketone, etc., nitriles such as acetonitrile and propionitrile, etc., carbonic acid esters such as methyl acetate or ethyl acetate, etc., alcohols such as methanol, ethanol or ethylene glycol, etc., amides such as N,N-dimethylformamide, N,N-dimethylacetamide and N-methyl-2-pyrrolidone, etc., water, and mixed solvents thereof.

The reaction temperature is generally −90 to 200° C., preferably −78 to 100° C.

The reaction time is generally 0.05 to 100 hours, preferably 0.5 to 10 hours.

[Reaction formula 15]

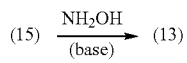

Reaction equation 15 shows the production of pyrazole-4-hydroxamic acid (13) used in Reaction formulae 7 and 12 to 14 by reacting pyrazole-4-carboxylic acid chloride (15) with hydroxyamine in the presence or absence of a base.

In this reaction, hydroxyamine is generally used in a molar amount of 1 to 100-fold, preferably 1 to 5-fold over (15).

The base used in this reaction includes inorganic bases such as sodium hydroxide, potassium hydroxide, potassium carbonate, sodium carbonate, potassium hydrogen carbonate, sodium hydrogen carbonate and sodium hydride, etc., organic bases such as pyridine, 4-dimethylamino pyridine, triethyl amine, N,N-dimethylaniline, 1,8-diazabicyclo[5.4.0]-7-undecene and 1,4-diazabicyclo[2.2.2]octane, etc., organic lithiums such as n-butyl lithium and sec-butyl lithium, etc., organic lithium amides such as lithium diisopropyl amide and lithium bis(trimethylsilyl)amide, etc., and metal alkoxides such as sodium methoxide, sodium ethoxide and potassium t-butoxide, etc. The base is generally used in a molar amount of 0 to 100-fold, preferably 0 to 5-fold over (15).

This reaction proceeds even without solvent, but a solvent can be used if necessary. The solvent is not specifically limited so long as it is inactive in this reaction, and includes for example hydrocarbons such as hexane, cyclohexane, benzene and toluene, etc., halogen-containing hydrocarbons such as carbon tetrachloride, chloroform and 1,2-dichloroethane, etc., ethers such as diethyl other, disopropyl ether, dioxane and tetrahydrofuran, etc., ketones such as acetonitrile, methyl ethyl ketone and methylisobutyl ketone, etc., nitriles such as acetonitrile and propionitrile, etc., amides such as N,N-dimethylformamide, N,N-dimethylacetamide and H-methyl-2-pyrrolidone, etc., water, and mixed solvents thereof.

The reaction temperature is generally −90 to 200° C., preferably 0 to 100° C.

The reaction time is generally 0.05 to 100 hours, preferably 0.5 to 10 hours.

The aimed products obtained according to the above-mentioned reactions can be isolated and purified by an operation such as filtering, extraction, washing, column chromatography, recrystallization and distillation, etc.

Hereinafter, synthetic examples of the compounds according to the present invention will be concretely described as examples and referential examples but the present invention is not limited thereto.

EXAMPLES

Example 1

Synthesis of N-((4,6-dimethoxypyrimidin-2-yl)aminocarbonyl)-3-chloro-1-methyl-4-(5-methyl-5H,6H-1,4,2-dioxadin-3-yl)pyrazole-5-sulfonamide (Compound No. 1 of the present invention)

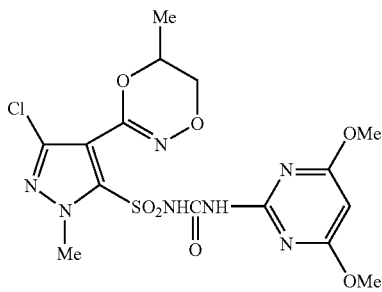

In acetonitrile (8 ml), 3-chloro-1-methyl-4-(5-methyl-5H,6H-1,4,2-dioxadin-3-yl)pyrazole-5-sulfonamide (0.64 g, 2.2 mmol) and N-(4,6-dimethoxypyrimidin-2-yl)carbamic acid phenyl (0.59 g, 2.1 mmol) were dissolved, 1,8-diazabicyclo[5.4.0]-7-undecene (0.33 g, 2.2 mmol) was added, and stirred at room temperature for 1 hour. After water (8 ml) was added, the mixture was extracted with diethyl ether. The resulting aqueous phase was adjusted to pH 1 by adding 12% hydrochloric acid, and re-extracted with diethyl ether. The resulting diethyl ether solution was washed with water and saturated sodium chloride aqueous solution in that order, then dried over anhydrous sodium sulfate and the solvent was distilled off. The resulting residue was washed with n-hexane, and dried to obtain the aimed product (0.40 g). Melting point 177-179° C. Proton nuclear magnetic resonance chemical shift values δ (ppm) (in CDCl$_3$) 1.38 (d, J=6.6 Hz, 3H), 3.69-3.72 (m, 1H), 3.96 (s, 6H), 4.13-4.18 (m, 1H), 4.30 (s, 3H), 4.49-4.63 (m, 1H), 5.77 (s, 1H), 7.67 (brs, 1H), 12.91 (brs, 1H).

Example 2

Synthesis of N-((4,6-dimethoxypyrimidin-2-yl)aminocarbonyl)-3-chloro-4-(5-iodomethyl-5H,6H-1,4,2-dioxadin-3-yl)-1-methylpyrazole-5-sulfonamide (Compound No. 2 of the present invention)

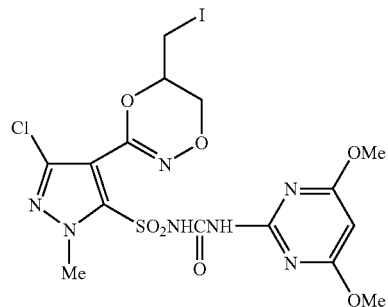

The procedure similar to that of Example 1 was carried by using 3-chloro-4-(5-iodomethyl-5H,6H-1,4,2-dioxadin-3-yl)-1-methylpyrazole-5-sulfonamide (0.090 g, 0.21 mmol) as a starting material to obtain the aimed product (0.10 g). Melting point 91-94° C. Proton nuclear magnetic resonance chemical shift values δ (ppm) (in CDCl$_3$) 3.28-3.42 (m, 2H), 3.89-4.05 (m, 7H), 4.04-4.12 (m, 1H), 4.31 (s, 3H), 4.56-4.60 (m, 1H), 5.79 (s, 1H), 7.43 (s, 1H), 12.93 (s, 1H).

Example 3

Synthesis of N-((4,6-dimethoxypyrimidin-2-yl)aminocarbonyl)-3-chloro-4-(5,5-dimethyl-5H,6H-1,4,2-dioxadin-3-yl)-1-ethylpyrazole-5-sulfonamide (Compound No. 3 of the present invention)

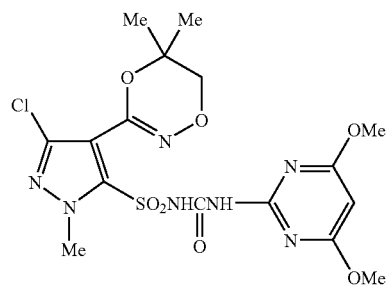

The procedure similar to that of Example 1 was carried by using 3-chloro-4-(5,5-dimethyl-5H,6H-1,4,2-dioxadin-3-yl)-1-methylpyrazole-5-sulfonamide (0.47 g, 1.5 mmol) as a starting material to obtain the aimed product (0.42 g). Melting point 189-191° C. Proton nuclear magnetic resonance chemical shift values δ (ppm) (in CDCl$_3$) 1.41 (s, 6H), 3.78 (s, 2H), 3.97 (s, 6H), 4.30 (s, 3H), 5.78 (s, 1H), 7.58 (brs, 1H), 12.92 (brs, 1H).

Example 4

Synthesis of N-(4,6-dimethoxypyrimidin-2-yl)aminocarbonyl)-3-chloro-4-(5 iodomethyl-5-methyl-5H, 6H-1,4,2-dioxadin-3-yl)-1-methylpyrazole-5-sulfonamide (Compound No. 4 of the present invention)

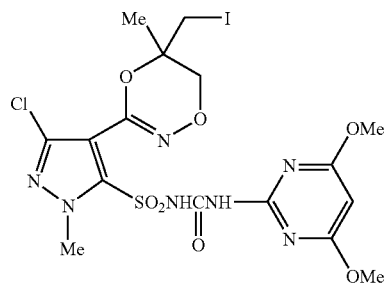

The procedure similar to that of Example 1 was carried by using 3-chloro-4-(5-iodomethyl-5-methyl-5H,6H-1,4,2-dioxadin-3-yl)-1-methylpyrazole-5-sulfonamide (0.21 g, 0.48 mmol) as a starting material to obtain the aimed product (0.14 g). Melting point 90-93° C. Proton nuclear magnetic resonance chemical shift values δ (ppm) (in CDCl$_3$) 1.55 (s, 3H), 3.30-3.49 (m, 2H), 3.81-3.84 (m, 1H), 3.97 (s, 6H), 4.23-4.30 (m, 4H), 5.80 (s, 1H), 7.29 (brs, 1H), 12.93 (brs, 1H).

Example 5

Synthesis of N-((4,6-dimethoxypyrimidin-2-yl)aminocarbonyl)-1,3-dimethyl-4-(5-methyl-5H,6H-1,4,2-dioxadin-3-yl)pyrazole-5-sulfonamide (Compound No. 5 of the present invention)

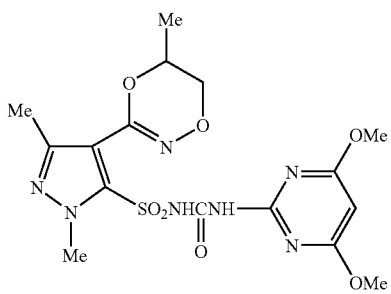

The procedure similar to that of Example 1 was carried by using 1,3-dimethyl-4-(5-methyl-5H,6H-1,4,2-dioxadin-3-yl)pyrazole-5-sulfonamide (0.070 g, 0.26 mmol) as a starting material to obtain the aimed product (0.090 g). Melting point 180-182° C. Proton nuclear magnetic resonance chemical shift values δ (ppm) (in CDCl$_3$) 1.36 (d, J=6.6 Hz, 3H), 2.99 (s, 3H), 3.2-3.69 (m, 1H), 3.97 (s, 6H), 4.11-4.16 (m, 1H), 4.27 (s, 3H), 4.49-4.54 (m, 1H), 5.78 (s, 1H), 7.23 (brs, 1H), 12.74 (brs, 1H).

Example 6

Synthesis of N-((4,6-dimethoxypyrimidin-2-yl)aminocarbonyl)-3-chloro-4-(5-iodomethyl-5H,6H-1,4,2-dioxadin-3-yl)-1-methylpyrazole-5-sulfonamide (Compound No. 6 of the present invention)

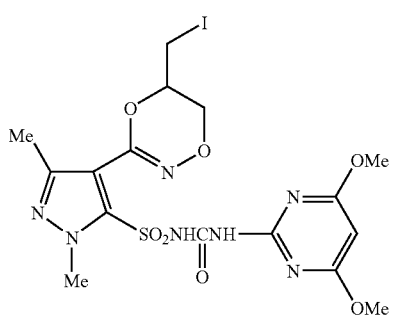

The procedure similar to that of Example 1 was carried by using 4-(5-iodomethyl-5H,6H-1,4,2-dioxadin-3-yl)-1,3-dimethylpyrazole-5-sulfonamide (0.53 g, 1.3 mmol) as a starting material to obtain the aimed product (0.34 g). Melting point 66-69° C. Proton nuclear magnetic resonance chemical shift values δ (ppm) (in CDCl$_3$) 2.34 (s, 3H), 3.36 (m, 2H), 3.92-4.19 (m, 8H), 4.23 (s, 3H), 4.54-4.59 (m, 1H), 5.78 (s, 1H), 7.41 (brs, 1H), 12.64 (brs, 1H).

Example 7

Synthesis of N-((4,6-dimethoxypyrimidin-2-yl)aminocarbonyl)-4-(5,5-dimethyl-5H,6H-1,4,2-dioxadin-3-yl)-1,3-dimethylpyrazole-5-sulfonamide (Compound No. 7 of the present invention)

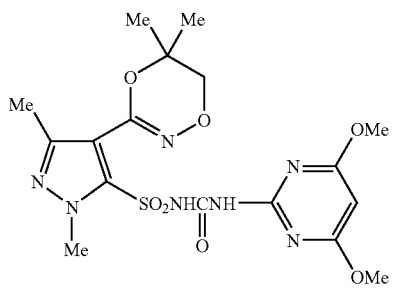

The procedure similar to that of Example 1 was carried by using 4-(5,5-dimethyl-5H,6H-1,4,2-dioxadin-3-yl)-1,3-dimethylpyrazole 6 sulfonamide (0.13 g, 0.45 mmol) as a starting material to obtain the aimed product (0.12 g). Melting point 199-201° C. Proton nuclear magnetic resonance chemical shift values δ (ppm) (in CDCl$_3$) 1.39 (s, 6H), 2.27 (s, 3H), 3.75 (s, 2H), 3.97 (s, 6H), 4.27 (s, 3H), 5.78 (s, 1H), 7.22 (brs, 1H), 12.75 (s, 1H).

Example 8

Synthesis of N-((4,6-dimethoxypyrimidin-2-yl)aminocarbonyl)-4-(5-iodomethyl-5-methyl-5H,6H-1,4,2-dioxadin-3-yl)-1,3-dimethylpyrazole-5-sulfonamide (Compound No. 8 of the present invention)

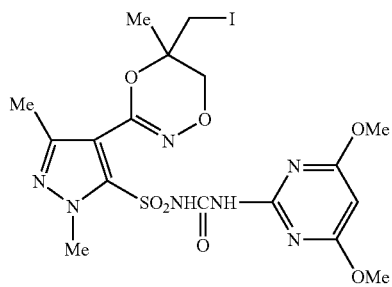

The procedure similar to that of Example 1 was carried by using 4-(5-iodomethyl-5-methyl-5H,6H-1,4,2-dioxadin-3-yl)-1,3-dimethylpyrazole-5-sulfonamide (0.080 g, 0.19 mmol) as a starting material to obtain the aimed product (0.050 g). Melting point 133-135° C. Proton nuclear magnetic resonance chemical shift values δ (ppm) (On CDCl$_3$) 1.63 (s, 3H), 2.29 (s, 3H), 3.31-3.46 (m, 2H), 3.78-3.82 (m, 1H), 3.97 (s, 6H), 4.17-4.27 (m, 4H), 5.79 (s, 1H), 7.40 (brs, 1H), 12.76 (brs, 1H).

Example 9

Synthesis of N-((4,6-dimethoxypyrimidin-2-yl)aminocarbonyl)-1,3-dimethyl-4-(6-methyl-5H,6H-1,4,2-dioxadin-3-yl)pyrazole-5-sulfonamide (Compound No. 9 of the present invention)

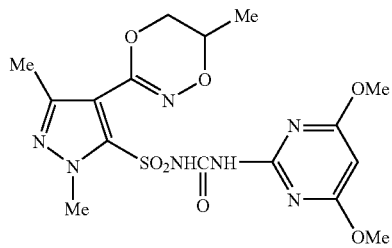

The procedure similar to that of Example 1 was carried by using 1,3-dimethyl-4-(6-methyl-5H,6H-1,4,2-dioxadin-3-yl)pyrazole-5-sulfonamide (0.14 g, 0.51 mmol) as a starting material to obtain the aimed product (0.17 g). Melting point 187-189° C. Proton nuclear magnetic resonance chemical shift values δ (ppm) (in CDCl$_3$) 1.28 (d, J=8.0 Hz, 3H), 2.29 (s, 3H), 3.96 (s, 6H), 3.99-4.04 (m, 2H), 4.27 (s, 3H), 4.29-4.33 (m, 1H), 5.78 (s, 1H), 7.26 (brs, 1H), 12.70 (brs, 1H).

Example 10

Synthesis of N-((4,6-dimethoxypyrimidin-2-yl)aminocarbonyl)-3-chloro-1-methyl-4-(5-methyl-5H,6H-1,4,2-dioxadin-3-yl)pyrazole-5-sulfonamide (Compound No. 1 of the present invention) (second version)

In toluene (100 ml), N-methoxycarbonyl-3-chloro-1-methyl-4-(5-methyl-5H,6H-1,4,2-dioxadin-3-yl)pyrazole-5-sulfonamide (20.3 g, 57.5 mmol) and 2-amino-4,6-dimethoxypyrimidine (9.40 g, 60.6 mmol) were added, and under reduced pressure (700 mmHg), refluxed under heating for 4 hours while methanol as by-product was distilled off. After 15 ml of toluene was distilled off at the same temperature, the mixture was cooled to room temperature with stirring. Precipitated solid was filtered off, washed with toluene and dried to obtain the aimed product (24.1 g). Melting point 177-179° C.

Example 11

Synthesis of N-((4,6-dimethoxypyrimidin-2-yl)aminocarbonyl)-3-chloro-1-methyl-4-(5-methyl-5H,6H-1,4,2-dioxadin-3-yl)pyrazole-5-sulfonamide (Compound No. 1 of the present invention) (third version)

In a solution of 2-amino-4,6-dimethoxypyrimidine (0.46 g, 3.0 mmol) in acetonitrile (3 ml), a solution of 3 chloro-1-methyl-4-(5-methyl-5H,6H-1,4,2-dioxadin-3-yl)pyrazole-5-sulfonylisocyanate (1.0 g, 3.1 mmol) in toluene (5 ml) was added, and stirred at room temperature for 3 hours. Precipitated solid was filtered off, washed with toluene and dried to obtain the aimed product (1.2 g). Melting point 177-179° C.

Example 12

Synthesis of N-((4,6-dimethoxypyrimidin-2-yl)aminocarbonyl)-3-chloro-1-methyl-4-(5-methyl-5H,6H-1,4,2-dioxadin-3-yl)pyrazole-5-sulfonamide (Compound No. 1 of the present invention) (fourth version)

In a solution of 2-amino-4,6-dimethoxypyrimidine (1.55 g, 10.0 mmol) in acetonitrile (15 ml), pyridine (0.16 g, 2.0 mol) and sodium cyanate (0.72 g, 11 mmol) were added, and with stirring, 3-chloro-1-methyl-4-(5-methyl-5H,6H-1,4,2-dioxadin-3-yl)pyrazole-5-sulfonyl chloride (3.45 g, 11.0 mmol) was added by portions over 1 hour at 40° C. At 40° C., the mixture was further stirred for 1.5 hour. After cooling to room temperature, water (60 ml) was added, the mixture was adjusted to pH 1 with 35% hydrochloric acid, and precipitated solid was filtered off. The resulting solid was washed with methanol and dried to obtain the aimed product (4.70 g). Melting point 177-179° C.

Example 13

Synthesis of N-((4,6-dimethoxypyrimidin-2-yl)aminocarbonyl)-1-methyl-4-(5-methyl-5H,6H-1,4,2-dioxadin-3-yl)pyrazole-5-sulfonamide (Compound No. 10 of the present invention)

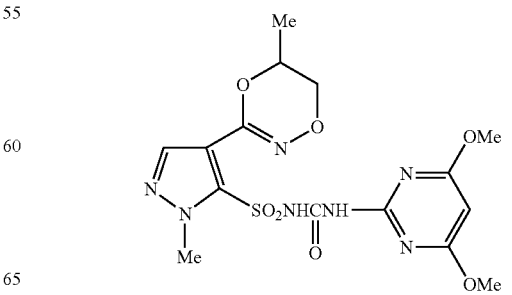

The procedure similar to that of Example 1 was carried by using 1-methyl-4-(5-methyl-5H,6H-1,4,2-dioxadin-3-yl) pyrazole-5-sulfonamide (0.20 g, 0.77 mmol) as a starting material to obtain the aimed product (0.25 g). Melting point 154-157° C. Proton nuclear magnetic resonance chemical shift values δ (ppm) (in CDCl$_3$) 1.35 (d, J=6.3 Hz, 3H), 3.56-3.64 (m, 1H), 4.03-4.13 (m, 7H), 4.34 (s, 3H), 4.44-4.50 (m, 1H), 5.78 (s, 1H), 7.45 (brs, 1H), 7.22 (s, 1H), 12.66 (brs, 1H).

Referential Example 1

(1) Synthesis of (5-benzylthio-3-chloro-1-methylpyrazol-4-yl)-N-allyloxycarboxylic acid amide

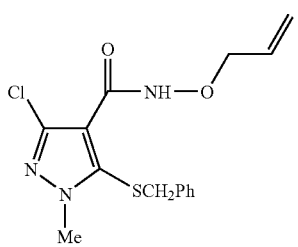

In a suspension of allyloxyamine hydrochloride (2.3 g, 21 mmol) in tetrahydrofuran (20 ml), 2.9 g (29 mmol) of triethylamine was added at 0° C., stirred at room temperature for 5 minutes and then a solution of 5-benzylthio-3-chloro-1-methylpyrazole-4-carboxylic acid chloride (2.1 g, 7.0 mmol) in tetrahydrofuran (10 ml) was added dropwise. After stirring at room temperature for 1 hour, water (100 ml) was added and extracted with ethyl acetate. The resulting ethyl acetate solution was washed with saturated sodium chloride aqueous solution, dried over anhydrous sodium sulfate and the solvent was distilled off to obtain the desired product (2.4 g). Oily substance. Proton nuclear magnetic resonance chemical shift values δ (ppm) (in CDCl$_3$) 3.45 (s, 3H), 4.11 (s, 2H), 4.53 (d, J=6.3 Hz, 2H), 5.34-5.45 (m, 2H), 6.00-6.13 (m, 1H), 7.03-7.06 (m, 2H), 7.24-7.28 (m, 3H), 9.14 (brs, 1H).

(2) Synthesis of 5-benzylthio-3-chloro-4-(5-iodomethyl-5H,6H-1,4,2-dioxadin-3-yl)-1-methylpyrazole

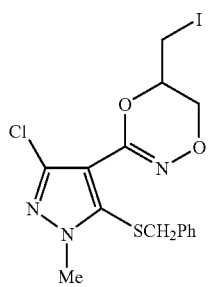

In a solution of (5-benzylthio-3-chloro-1-methylpyrazol-4-yl)-N-allyloxycarboxylic acid amide (2.2 g, 6.5 mmol) in acetonitrile (70 ml), iodine (5.0 g, 20 mmol) was added at 0° C. After stirring at room temperature for 6 hours, water (150 ml) was added, and extracted with ethyl acetate. The resulting ethyl acetate solution was washed with saturated sodium thiosulfate aqueous solution, saturated sodium hydrogen carbonate aqueous solution, saturated sodium chloride aqueous solution and water in that order, dried over anhydrous sodium sulfate and the solvent was distilled off to obtain the desired product (3.0 g). Oily substance. Proton nuclear magnetic resonance chemical shift values δ (ppm) (in CDCl$_3$) 3.25 (s, 3H), 3.34-3.42 (m, 2H), 4.04-4.11 (m, 3H), 4.32-4.40 (m, 1H), 4.58-4.65 (m, 1H), 7.00-7.08 (m, 2H), 7.21-7.27 (m, 3H).

(3) Synthesis of 5-benzylthio-3-chloro-1-methyl(5-methyl-5H,6H-1,4,2-dioxadin-3-yl)pyrazole

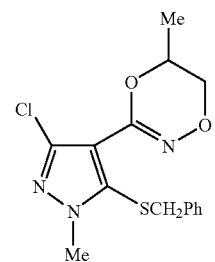

In a solution of 5-benzylthio-3-chloro-4-(5-iodomethyl-5H,6H-1,4,2-dioxadin-3-yl)-1-methylpyrazole (2.9 g, 6.3 mmol) in dimethylsulfoxide (40 ml), sodium boron hydride (0.47 g, 12 mmol) was added. After stirring at 60° C. for 0.6 hour, 6% hydrochloric acid (200 ml) was added, and extracted with ethyl acetate. The resulting ethyl acetate solution was washed with saturated sodium chloride aqueous solution and water in that order, dried over anhydrous sodium sulfate and the solvent was distilled off to obtain the desired product (2.0 g). Oily substance. Proton nuclear magnetic resonance chemical shift values δ (ppm) (in CDCl$_3$) 1.44 (d, J=6.6 Hz, 3H), 3.24 (s, 3H), 3.74-3.85 (m, 1H), 4.04 (s, 2H), 4.22-4.29 (m, 1H), 4.56-4.65 (m, 1H), 6.97-7.06 (m, 2H), 7.19-7.21 (m, 3H).

(4) Synthesis of 3-chloro-1-methyl-4-(5-methyl-5H, 6H-1,4,2-dioxadin-3-yl)pyrazole-5-sulfonamide

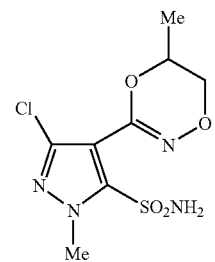

In a solution of 5-benzylthio-3-chloro-1-methyl-4-(5-methyl-5H,6H-1,4,2-dioxadin-3-yl)pyrazole (1.9 g, 5.6 mmol) in methylene chloride (30 ml), water (30 ml) and 35% hydrochloric acid (2.3 g, 22 mmol) were added, and 8% sodium hypochlorite aqueous solution (20.5 g, 22.0 mmol) was added with vigorously stirring at 5° C., and stirred for 0.5 hour. After excluding excess chlorine by introducing nitrogen, water (50 ml) was added, and extracted with methylene chloride. The resulting methylene chloride solution was concentrated under reduced pressure, and then the residue was dissolved in tetrahydrofuran (8 ml), 28% ammonia water (5 ml) was added at 0° C., and stirred at room temperature for 0.25 hour. Water (20 ml) was added, extracted with diethyl ether, and the diethyl ether phase was discarded. After adjusting to pH 1 by adding 35% hydrochloric acid in the resulting aqueous phase, the phase was extracted with diethyl ether again. The resulting diethyl ether solution was washed with saturated sodium chloride aqueous solution, and then dried over anhydrous sodium sulfate, and the solvent was distilled off to obtain the aimed product (0.64 g). Melting point 120-122° C. Proton nuclear magnetic resonance chemical shift values δ (ppm) (in $CDCl_3$) 1.43 (d, J=6.3 Hz, 3H), 3.74-3.80 (m, 1H), 4.13 (s, 3H), 4.21-4.26 (m, 1H), 4.57-4.67 (m, 1H), 6.12 (brs, 2H).

Referential Example 2

Synthesis of 3-chloro-4-(5-iodomethyl-5H,6H-1,4,2-dioxadin-3-yl)-1-methylpyrazol-5-sulfonamide

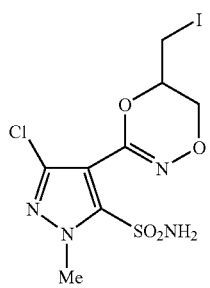

The procedure similar to that of (4) in Referential Example 1 was carried by using 5-benzylthio-3-chloro-4-(5-iodomethyl-5H,6H-1,4,2-dioxadin-3-yl)-1-methylpyrazole (0.24 g, 0.52 mmol) as a starting material to obtain the aimed product (0.090 g). Solid.

Referential Example 3

(1) Synthesis of (5-benzylthio-3-chloro-1-methylpyrazol-4-yl)-N-(2-methyl-2-propenyloxy)carboxylic acid amide

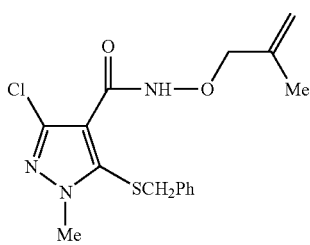

The procedure similar to that of (1) in Referential Example 1 was carried by using 2-methyl-2-propenyloxyamine hydrochloride (1.2 g, 9.7 mmol) as a starting material to obtain the aimed product (1.8 g). Oily substance. Proton nuclear magnetic resonance chemical shift values δ (ppm) (in $CDCl_3$) 1.88 (8, 3H), 3.36 (s, 3H), 4.11 (s, 2H), 4.45 (s, 2H), 5.08 (d, J=9.9 Hz, 2H), 7.01-7.06 (m, 2H), 7.22-7.28 (m, 3H), 9.15 (brs, 1H).

(2) Synthesis of 5-benzylthio-3-chloro-4-(5-iodomethyl-5-methyl-5H,6H-1,4,2-dioxadin-3-yl-1-methylpyrazole

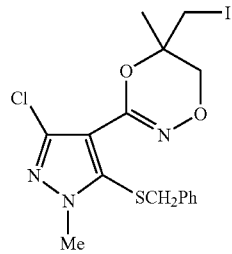

The procedure similar to that of (2) in Referential Example 1 was carried by using (5-benzylthio-3-chloro-1-methylpyrazol-4-yl)-N-(2-methyl-2-propenyloxy)carboxylic acid amide (1.7 g, 4.8 mmol) as a starting material to obtain the aimed product (2.3 g). Oily substance. Proton nuclear magnetic resonance chemical shift values δ (ppm) (in $CDCl_3$) 1.61 (s, 3H), 3.23 (s, 3H), 3.39-3.55 (m, 2H), 3.91-3.95 (m, 1H), 4.11 (s, 2H), 4.25-4.29 (m, 1H), 6.98-7.06 (m, 2H), 7.21-7.28 (m, 3H).

(3) Synthesis of 5-benzylthio-3-chloro-1-methyl-(5,5-dimethyl-5H,6H-1,4,2-dioxadin-3-yl)pyrazole

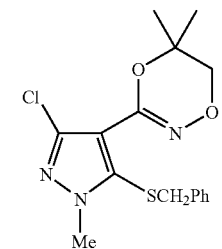

The procedure similar to that of (3) in Referential Example 1 was carried by using (5-benzylthio-3-chloro-4-(5-iodomethyl-5-methyl-5H,6H-1,4,2-dioxadin-3-yl)-1-methylpyrazole (1.7 g, 3.6 mmol) as a starting material to obtain the aimed product (1.3 g). Oily substance. Proton nuclear magnetic resonance chemical shift values δ (ppm) (in $CDCl_3$) 1.48 (s, 6H), 3.23 (s, 3H), 3.88 (s, 2H), 4.05 (s, 2H), 6.99-7.06 (m, 2H), 7.21-7.28 (m, 3H).

(4) Synthesis of 3-chloro-1-methyl-4-(5,5-dimethyl-5H,6H-1,4,2-dioxadin-3-yl)pyrazole-5-sulfonamide

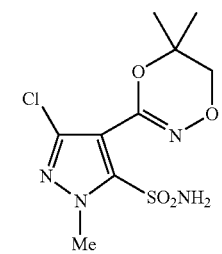

The procedure similar to that of (4) in Referential Example 1 was carried by using 5-benzylthio-3-chloro-1-methyl-4-(5, 5-dimethyl-5H,6H-1,4,2-dioxadin-3-yl)pyrazole (1.2 g, 3.4 mmol) as a starting material to obtain the aimed product (0.47 g). Solid.

Referential Example 4

Synthesis of 3-chloro-4-(5-iodomethyl-5H,6H-1,4,2-dioxadin-3-yl)-1-methylpyrazole-5-sulfonamide

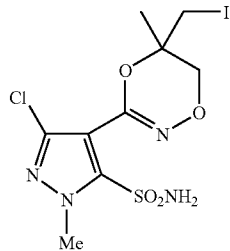

The procedure similar to that of (4) in Referential Example 1 was carried by using 5-benzylthio-3-chloro-4-(5-iodomethyl-5-methyl-5H,6H-1,4,2-dioxadin-3-yl)-1-methylpyrazole (0.50 g, 1.0 mmol) as a starting material to obtain the aimed product (0.21 g). Solid.

Referential Example 5

(1) Synthesis of (5-benzylthio-1,3-dimethylpyrazol-4-yl)-N-allyloxy carboxylic acid amide

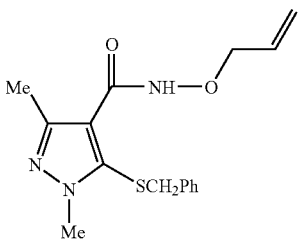

The procedure similar to that of (1) in Referential Example 1 was carried by using 5-benzylthio-1,3-dimethylpyrazole-4-carboxylic acid chloride (1.6 g, 5.7 mmol) as a starting material to obtain the aimed product (1.5 g). Oily substance. Proton nuclear magnetic resonance chemical shift values δ (ppm) (in CDCl$_3$) 2.50 (s, 3H), 3.34 (s, 3H), 3.92 (s, 2H), 4.48-4.51 (m, 2H), 5.32-5.43 (m, 2H), 6.02-6.11 (m, 1H), 6.96-7.00 (m, 2H), 7.23-7.30 (m, 3H), 9.77 (s, 1H).

(2) Synthesis of 5-benzylthio-4-(5-iodomethyl-5H, 6H-1,4,2-dioxadin-3-yl)-1,3-dimethylpyrazole

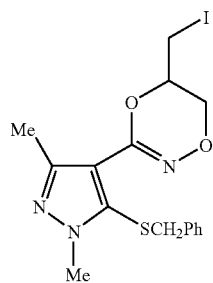

The procedure similar to that of (2) in Referential Example 1 was carried by using (5-benzylthio-1,3-dimethylpyrazol-4-yl)-N-allyloxycarboxylic acid amide (0.92 g, 2.9 mmol) as a starting material to obtain the aimed product (0.74 g). Melting point 79-81° C. Proton nuclear magnetic resonance chemical shift values δ (ppm) (in CDCl$_3$) 2.37 (s, 3H), 3.29 (s, 3H), 3.36-3.40 (m, 2H), 3.97-4.04 (m, 3H), 4.29-4.34 (m, 1H), 4.53-4.60 (m, 1H), 7.00-7.06 (m, 2H), 7.20-7.28 (m, 3H).

(3) Synthesis of 5-benzylthio-1.3-dimethyl-4-(5-methyl-5H,6H-1,4,2-dioxadin-3-yl)pyrazole

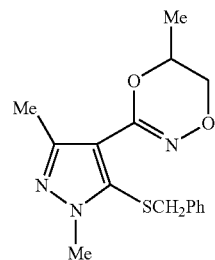

The procedure similar to that of (3) in Referential Example 1 was carried by using 5-benzylthio-4-(5-iodomethyl-5H,6H-1,4,2-dioxadin-3-yl)-1,3-dimethylpyrazole (0.71 g, 1.6 mmol) as a starting material to obtain the aimed product (0.19 g). Oily substance.

(4) Synthesis of 1.3-dimethyl-4-(5-methyl-5H,6H-1,4,2-dioxadin-3-yl)pyrazole-5-sulfonamide

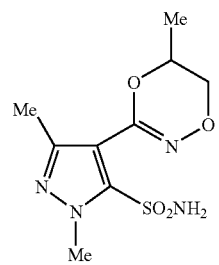

The procedure similar to that of (4) in Referential Example 1 was carried by using 5-benzylthio-1,3-dimethyl-4-(5-methyl-5H,6H-1,4,2-dioxadin-3-yl)pyrazole (0.19 g, 0.6 mmol) as a starting material to obtain the aimed product (0.070 g). Solid. Proton nuclear magnetic resonance chemical shift values δ (ppm) (in CDCl$_3$) 1.42 (s, 3H), 2.33 (s, 3H), 3.71-3.78 (m, 1H), 4.10 (s, 3H), 4.21-4.25 (m, 1H), 4.60 (m, 1H), 6.15 (s, 2H).

Referential Example 6

Synthesis of 4-(5-iodomethyl-5H,6H-1,4,2-dioxadin-3-yl)-1,3-dimethylpyrazol-5-sulfonamide

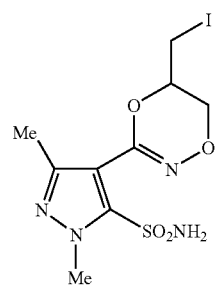

The procedure similar to that of (4) in Referential Example 1 was carried by using 5-benzylthio-4-(5-iodomethyl-5H,6H-1,4,2-dioxadin-3-yl)-1,3-dimethylpyrazole (0.70 g, 1.6 mmol) as a starting material to obtain the aimed product (0.53 g). Solid.

Referential Example 7

(1) Synthesis of (5-benzylthio-1,3-dimethylpyrazol-4-yl)-N-(2-methyl-2-propenyloxy) carboxylic acid amide

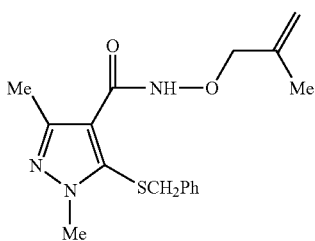

The procedure similar to that of (1) in Referential Example 1 was carried by using 5-benzylthio-1,3-dimethylpyrazole-carboxylic acid chloride (1.10 g, 3.9 mmol) and 2-methyl-2-propenyloxy amine hydrochloride (1.30 g, 10.5 mmol) as starting materials to obtain the aimed product (1.159). Oily substance. Proton nuclear magnetic resonance chemical shift values δ (ppm) (in CDCl₃) 1.89 (s, 3H), 2.51 (s, 3H), 3.33 (s, 3H), 3.91 (s, 2H), 4.42 (s, 2H), 5.06 (d, J=11.3 Hz, 2H), 6.95-7.01 (m, 2H), 7.24-7.29 (m, 3H), 9.77 (brs, 1H).

(2) Synthesis of 5-benzylthio-(5-iodomethyl-5-methyl-5H,6H-1,4,2-dioxadin-3-yl)-1,3-dimethylpyrazole

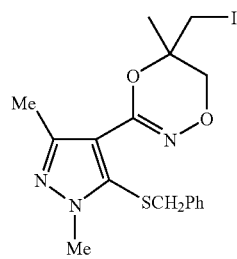

The procedure similar to that of (2) in Referential Example 1 was carried by using (5-benzylthio-1,3-dimethylpyrazol-4-yl)-N-(2-methyl-2-propenyloxy)carboxylic acid amide (0.60 g, 1.8 mmol) as a starting material to obtain the aimed product (0.78 g). Oily substance. Proton nuclear magnetic resonance chemical shift values δ (ppm) (in CDCl₃) 1.60 (s, 3H), 2.37 (s, 3H), 3.27 (s, 3H), 3.39-3.52 (m, 2H), 3.88-3.93 (m, 1H), 4.00 (s, 2H), 4.19-4.24 (m, 1H), 7.00-7.05 (m, 2H), 7.20-7.24 (m, 3H).

(3) Synthesis of 5-benzylthio-1.3-dimethyl-4-(5,5-dimethyl-5H,6H-1,4,2-dioxadin-3-yl)pyrazole

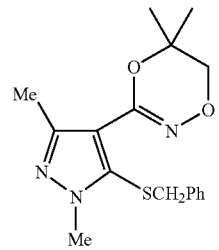

The procedure similar to that of (3) in Referential Example 1 was carried by using 5-benzylthio-4-(5-iodomethyl-5-methyl-5H,6H-1,4,2-dioxadin-3-yl)-1,3-dimethylpyrazole (0.54 g, 1.2 mmol) as a starting material to obtain the aimed product (0.38 g). Oily substance. Proton nuclear magnetic resonance chemical shift values δ (ppm) (in CDCl₃) 1.47 (s, 6H), 2.34 (s, 3H), 3.26 (s, 3H), 3.86 (s, 2H), 4.00 (s, 2H), 6.98-7.05 (m, 2H), 7.21-7.25 (m, 3H).

(4) Synthesis of 1.3-dimethyl-4-(5,5-dimethyl-5H,6H-1,4,2-dioxadin-3-yl)pyrazole-5-sulfonamide

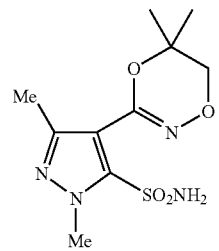

The procedure similar to that of (4) in Referential Example 1 was carried by using 5-benzylthio-1,3-dimethyl-4-(5,5-dimethyl-5H,6H-1,4,2-dioxadin-3-yl)pyrazole (0.34 g, 1.0 mmol) as a starting material to obtain the aimed product (0.13 g). Solid.

Referential Example 8

Synthesis of 4-(5-iodomethyl-5-methyl-5H,6H-1,4,2-dioxadin-3-yl)-1,3-dimethylpyrazole-5-sulfonamide

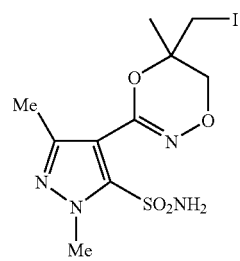

The procedure similar to that of (4) in Referential Example 1 was carried by using 5-benzylthio-4-(5-iodomethyl-5-methyl-5H,6H-1,4,2-dioxadin-3-yl)-1,3-dimethylpyrazole (0.20 g, 0.44 mmol) as a starting material to obtain the aimed product (0.080 g). Solid.

Referential Example 9

(1) Synthesis of ethyl 2-(1,3-dimethyl-5-benzylthi-opyrazol-4-yl)carbonylaminoxy) propanoate

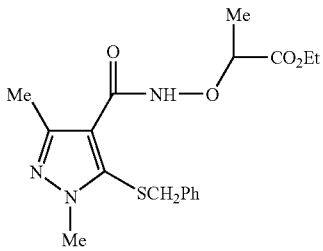

In a solution of 5-benzylthio-3-chloro-1-methyl-pyrazole-4-carboxylic acid (1.0 g, 3.8 mmol) in methylene chloride (20 ml), ethyl 2-aminooxypropanoate (0.58 g, 4.4 mmol) and N-ethyl-N'-(3-dimethylaminopropyl)carbodiimide hydrochloride (0.83 g, 4.3 mmol) were added, and stirred at room temperature for 12 hours. After distilling out the solvent under reduced pressure, water (50 ml) was added and extracted with ethyl acetate. The resulting ethyl acetate solution was washed with saturated sodium chloride aqueous solution, dried over anhydrous sodium sulfate, and the solvent was distilled off. The resulting residue was purified with silica gel column chromatography (developing solution: n-hexane/ethyl acetate=1/1) to obtain 0.88 g of the aimed product. Oily substance. Proton nuclear magnetic resonance chemical shift values δ (ppm) (in CDCl$_3$) 1.30 (t, J=8 Hz, 3H), 1.57 (d, J=10 Hz, 3H), 2.47 (s, 3H), 3.28 (s, 3H), 3.40 (q, J=8 Hz, 2H), 4.18-4.32 (m, 2H), 4.62-4.71 (m, 1H), 6.91-7.07 (m, 2H), 7.15-7.31 (m, 3H), 10.40 (s, 1H).

(2) Synthesis of (1,3-dimethyl-5-benzylthiopyrazol-4-yl)-N-(2-hydroxyisopropoxy)carboxylic acid amide

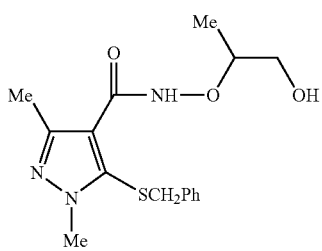

In a suspension of lithium aluminum hydride (0.090 g, 2.4 mmol) in diethyl ether (20 ml), a solution of ethyl 2-(1,3-dimethyl-5-benzylthiopyrazol-4-yl)carbonylaminooxy)propanoate (0.88 g, 2.3 mmol) in diethyl ether (5 ml) was added dropwise with stirring. After stirring at the same temperature for 2.5 hours, the reaction solution was poured in ice water (20 ml), adjusted to pH 1 by adding 10% hydrochloric acid, and extracted with ethyl acetate. The ethyl acetate solution was washed with water, dried over anhydrous sodium sulfate and the solvent was distilled off to obtain the desired product (0.70 g). Oily substance. Proton nuclear magnetic resonance chemical shift values δ (ppm) (in CDCl$_3$) 1.29 (d, J=8 Hz, 3H), 2.74 (s, 3H), 3.26-3.50 (m, 1H), 3.42 (s, 3H), 3.59-3.72 (m, 1H), 3.94 (s, 2H), 3.96-4.03 (m, 1H), 4.72 (brs, 1H), 6.91-7.02 (m, 2H), 7.20-7.32 (m, 3H), 9.60 (brs, 1H).

(3) Synthesis of 5-benzylthio-1,3-dimethyl-4-(6-methyl-5H,6H-1,4,2-dioxadin-3-yl)pyrazole

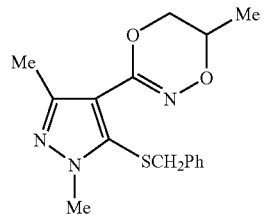

In a solution of (1,3-dimethyl-5-benzylthiopyrazol-4-yl)-N-(2 hydroxyisopropoxy)carboxylic acid amide (0.70 g, 2.1 mmol) in methylene chloride (5 ml), thionyl chloride (0.34 ml, 4.6 mmol) was added, refluxed for 1.5 hour and then the solvent was distilled off. The resulting residue was dissolved in N,N-dimethylformamide (10 ml), 55% sodium hydride (0.10 g, 2.3 mmol) was added at 5° C., and further stirred at the same temperature for 1 hour Water (20 ml) was added, extracted with ethyl acetate, and the resulting ethyl acetate solution was washed with saturated sodium chloride aqueous solution, dried over anhydrous sodium sulfate, and the solvent was distilled off. The resulting residue was purified with silica gel column chromatography (developing solution: n-hexane/ethyl acetate=1/1) to obtain the aimed product (0.32 g). Solid. Proton nuclear magnetic resonance chemical shift values δ (ppm) (in CDCl$_3$) 1.37 (t, J=8 Hz, 3H), 2.33 (s, 3H), 3.28 (s, 3H), 3.95-4.05 (m, 2H), 4.08-4.13 (m, 1H), 4.44-4.51 (m, 1H), 6.99-7.08 (m, 2H), 7.09-7.15 (m, 3H).

(4) Synthesis of 1,3-dimethyl-4-(6-methyl-5H,6H-1,4,2-dioxadin-3-yl)pyrazole-5-sulfonamide

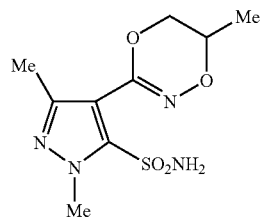

The procedure similar to that of (4) in Referential Example 1 was carried by using 5-benzylthio-1,3-dimethyl-4-(6-methyl-5H,6H-1,4,2-dioxadin-3-yl)pyrazole (0.32 g, 1.0 mmol) as a starting material to obtain the aimed product (0.14 g). Solid.

Referential Example 10

(1) Synthesis of 3,5-dichloro-1-methylpyrazole-4-carbohydroxamic acid

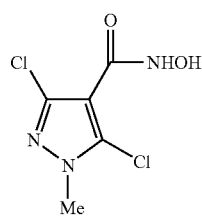

In a solution of hydroxyamine hydrochloride (106.9 g, 1.538 mol) in water (200 ml), a solution of 85% potassium hydroxide (101.5 g, 1.538 mol) in water (200 ml) was added at 5 to 15° C., and stirred at room temperature for 5 minutes. Then, a solution of 3,5-dichloro-1-methylpyrazole-4-carboxylic acid chloride (100.0 g, 0.5128 mol) in tetrahydrofuran (170 ml) was added dropwise at 3 to 8° C. over 2 hours. After stirring at 5° C. for 0.5 hour, the mixture was adjusted to pH 3-4 by adding 35% hydrochloric acid. Precipitated solid was filtered off, washed with water, and dried to obtain the aimed product (94.9 g). Melting point 200-202° C. (decomposition). Proton nuclear magnetic resonance chemical shift values δ (ppm) (in dimethylsulfoxide-$d_6$) 3.79 (s, 3H), 9.24 (brs, 1H), 10.83 (brs, 1H).

(2) Synthesis of N-allyloxy-3,5-dichloro-1-methylpyrazole-4-carboxylic acid amide

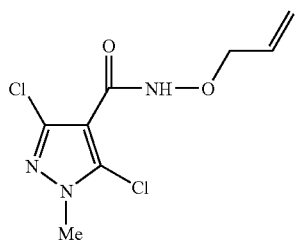

In a solution of potassium carbonate (15.8 g, 114 mmol) in water (60 ml), a solution of 3,5-dichloro-1-methylpyrazole-4-carbohydroxamic acid (20.0 g, 95.2 mmol) and allyl bromide (13.8 g, 114 mmol) in toluene (60 ml) was added, and stirred at 50° C. for 3 hours. After cooling to room temperature, the mixture was adjusted to pH 1 by adding 35% hydrochloric acid, precipitated solid was filtered off, washed with water and toluene in that order, and dried to obtain the aimed product (17.2 g). Melting point 96-97° C. Proton nuclear magnetic resonance chemical shift values δ (ppm) (in $CDCl_3$) 3.84 (s, 3H), 4.51 (d, J=6.3 Hz, 2H), 5.3-5.46 (m, 2H), 5.94-6.13 (m, 1H), 8.80 (brs, 1H).

(3) Synthesis of 3,5-dichloro-4-(5-iodomethyl-5H,6H-1,4,2-dioxadin-3-yl)-1-methylpyrazole

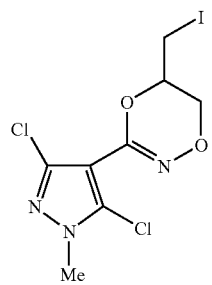

In a solution of N-allyloxy-3,5-dichloro-1-methylpyrazole-4-carboxylic acid amide (40.0 g, 160 mmol) in acetonitrile (200 ml), iodine (122 g, 481 mmol) was added, and stirred at room temperature for 4.5 hours. Saturated sodium thiosulfate aqueous solution (150 ml) was added, extracted with ethyl acetate, the resulting ethyl acetate solution was washed with saturated sodium hydrogen carbonate, saturated sodium chloride aqueous solution and water in that order, dried over anhydrous sodium sulfate, and the solvent was distilled off. The resulting residue was purified with silica gel column chromatography (developing solution: n-hexane/ethyl acetate=5/2) to obtain the aimed product (54.0 g). Oily substance. Proton nuclear magnetic resonance chemical shift values δ (ppm) (In $CDCl_3$) 3.37 (d, J=6.9 Hz 2H), 3.83 (s, 3H), 3.99-4.06 (m, 1H), 4.32-4.38 (m, 1H), 4.54-4.62 (m, 1H).

(4) Synthesis of 3,5-dichloro-1-methyl-4-(5-methyl-5H,6H-1,4,2-dioxadin-3-yl)pyrazole (first version)

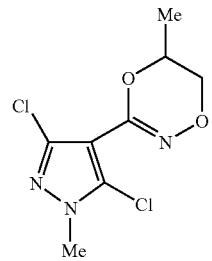

In a solution of sodium boron hydride (0.30 g, 7.9 mmol) in N,N-dimethylformamide (15 ml), 3,5-dichloro-4-(5-iodomethyl-5H,6H-1,4,2-dioxadin-3-yl)-1-methylpyrazole (2.0 g, 5.3 mmol) was added, and stirred at 60° C. for 0.5 hour. After cooling to room temperature, water (10 ml) was added, and further 35% hydrochloric acid was added to adjust to pH 1, and extracted with ethyl acetate. The resulting ethyl acetate solution was washed with saturated sodium hydrogen carbonate, saturated sodium chloride aqueous solution and water in that order, dried over anhydrous sodium sulfate, and the solvent was distilled off. The resulting residue was purified with silica gel column chromatography (developing solution: n-hexane/ethyl acetate=5/2) to obtain the aimed product (1.1 g). Melting point 50-51° C. Boiling point 142° C./0.3 mmHg. Proton nuclear magnetic resonance chemical shift values δ (ppm) (in $CDCl_3$) 1.41 (d, J=6.3 Hz, 3H), 3.69-3.76 (m, 1H), 3.82 (s, 3H), 4.20-4.26 (m, 1H), 4.52-4.61 (m, 1H).

(5) Synthesis of 3-chloro-5-mercapto-1-methyl-4-(5-ethyl-5H,6H-1,4,2-dioxadin-3-yl) pyrazole

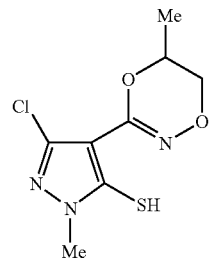

In a suspension of 70% sodium hydrosulfide (4.3 g, 54 mmol) in N,N-dimethylformamide (38 ml), 3,5-dichloro-1-methyl-4-(5-methyl-5H,6H-1,4,2-dioxadin-3-yl)pyrazole (3.8 g, 15 mmol) was added, and stirred at 80° C. for 5.5 hours. After cooling to room temperature, water (50 ml) was added, and insoluble products were filtered off. The filtrate was adjusted to pH 1 by adding 35% hydrochloric acid, precipitated solid was filtered off, washed with water, and dried to obtain the aimed product (2.55 g). Melting point 60-64° C.

Proton nuclear magnetic resonance chemical shift values δ (ppm) (in CDCl₃) 1.48 (d, J=6.3 Hz, 3H), 3.75 (s, 3H), 3.79-3.85 (m, 1H), 4.28-4.32 (m, 1H), 4.64-474 (m, 1H).

(6) Synthesis of 3-chloro-1-methyl-4-(5-methyl-5H,6H-1,4,2-dioxadin-3-yl)pyrazole-5-sulfonyl chloride

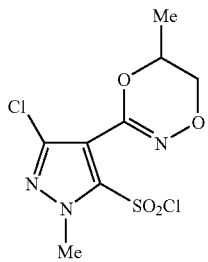

In a solution of 3-chloro-5-mercapto-1-methyl-4-(5-methyl-5H,6H-1,4,2-dioxadin-3-yl)pyrazole (2.5 g, 10 mmol) In 1,2-dichloroethane (50 ml), water (20 ml) was added, and under ice cooling, chlorine (2.1 g, 30 mmol) was introduced with vigorously stirring. In this process the temperature rised to 20° C. After excluding excess chlorine by introducing nitrogen, 1,2-dichloroethane phase was separated. The resulting 1,2-dichloroethane solution was wished with saturated sodium hydrogen sulfite aqueous solution and water in that order, and then dried over anhydrous sodium sulfate, and the solvent was distilled off to obtain the aimed product (3.1 g). Melting point 63-68° C. Proton nuclear magnetic resonance chemical shift values δ (ppm) (in CDCl₃) 1.41 (d, J=6.3 Hz, 3H), 3.75-3.81 (m, 1H), 4.20 (s, 3H), 4.23-4.28 (m, 1H), 4.54-4.64 (m, 1H).

(7) Synthesis of 3-chloro-1-methyl-4-(5-methyl-5H,6H-1,4,2-dioxadin-3-yl)pyrazole-5-sulfonamide (second version)

In a solution of 3-chloro-1-methyl-4-(5-methyl-5H,6H-1,4,2-dioxadin-3-yl)pyrazole-5-sulfonyl chloride (3.1 g, 9.9 mmol) In 1,2-dichloroethane (30 ml), 28% ammonia water (1.5 g, 24.7 mmol) was added dropwise with vigorously stirring under ice cooling. After stirring at room temperature for 0.5 hour, water (20 ml) and 35% hydrochloric acid (5.2 g, 50 mmol) were added, and extracted with 1,2-dichloroethane. The resulting 1,2-dichloroethane solution was washed with water, dried over anhydrous sodium sulfate, and the solvent was distilled off to obtain the aimed product (2.8 g). Melting point 120-122° C.

(8) Synthesis of N-methoxycarbonyl-3-chloro-1-methyl-4-(5-methyl-5H,6H-1,4,2-dioxadin-3-yl)pyrazole-5-sulfonamide

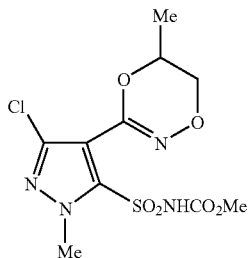

In a solution of 3-chloro-1-methyl-4-(5-methyl-5H,6H-1,4,2-dioxadin-3-yl)pyrazole-5-sulfonamide (3.0 g, 10 mmol) in acetonitrile (15 ml), anhydrous potassium carbonate (1.8 g, 13 mmol) and methyl chloroformate (0.96 g, 10 mmol) were added, and refluxed under heating for 1 hour. Under reduced pressure, the residue obtained by distilling off the solvent was dissolved in water (20 ml), insoluble materials were filtered off, and then extracted with 1,2-dichloroethane. The resulting aqueous phase was adjusted to pH 1 by adding 35% hydrochloric acid, precipitated solid was filtered off, washed with water and dried to obtain the aimed product (2.4 g). Melting point 133-134° C. Proton nuclear magnetic resonance chemical shift values δ (ppm) (in CDCl₃) 1.43 (d, J=6.6 Hz, 3H), 3.72 (s, 3H), 3.74-3.81 (m, 1H), 4.21-4.30 (m, 1H), 4.25 (s, 3H), 4.56-4.68 (m, 1H), 8.83 (brs, 1H).

Referential Example 11

(1) Synthesis of 3,5-dichloro-1-methyl-4-(5-methylene-5H,6H-1,4,2-dioxadin-3-yl)pyrazole

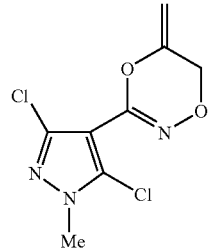

In a solution of 3,5-dichloro-4-(5-iodomethyl-5H,6H-1,4,2-dioxadin-3-yl)-1-methylpyrazole (1.5 g, 4.0 mmol) in tetrahydrofuran (10 ml), potassium t-butoxide (0.52 g, 4.6 mmol) was added, and stirred at room temperature for 0.25 hour. Saturated ammonium chloride aqueous solution (20 ml) was added, extracted with ethyl acetate, the resulting ethyl acetate solution was washed with water and saturated sodium chloride aqueous solution in that order, dried over anhydrous sodium sulfate, and the solvent was distilled off. The resulting residue was purified with silica gel column chromatography (developing solution: n-hexane/ethyl acetate=1/1) to obtain the aimed product (0.88 g). Melting point 68-70° C. Proton nuclear magnetic resonance chemical shift values δ (ppm) (in CDCl₃) 3.84 (s, 3H), 4.42 (s, 2H), 4.45 (d, J=1.8 Hz, 1H), 4.85 (d, J=1.8 Hz, 1H).

(2) Synthesis of 3,5-dichloro-1-methyl-4-(5-methyl-5H,6H-1,4,2-dioxadin-3-yl)pyrazole (second version)

In a solution of 3,5-dichloro-1-methyl-4-(5-methylene-5H,6H-1,4,2-dioxadin-3-yl)pyrazole (2.8 g, 11 mmol) in ethyl acetate (58 ml), 5% palladium-carbon (0.56 g) was added, and under hydrogen atmosphere (1 atm), the mixture was stirred at room temperature for 17 hours. 5% palladium-carbon (0.05 g) was further added, and further stirred under the abovementioned condition for 1 hour, and the catalyst was filtered off. The solvent was distilled off from the filtrate, and the resulting residue was purified with alumina column chromatography (developing solution: chloroform) to obtain the aimed product (2.6 g). Melting point 50-51° C.

Referential Example 12

Synthesis of 3,5-dichloro-1-methyl-4-(5-methyl-5H, 6H-1,4,2-dioxadin-3-yl)pyrazole (third version)

In a solution of N-allyloxy-3,5-dichloro-1-methylpyrazole-4-carboxylic acid amide (0.50 g, 2.0 mmol) in toluene (5 ml), trifluoromethane sulfonic acid (0.10 g, 1.04 mmol) was added, and refluxed for 20 hours. The resulting toluene solution was washed with saturated potassium carbonate aqueous solution and water in that order, dried over anhydrous sodium sulfate, and the solvent was distilled off. The resulting residue was purified with silica gel column chromatography (developing solution: n-hexane/ethyl acetate=1/1) to obtain the aimed product (0.08 g). Melting point 50-51° C.

Referential Example 13

(1) Synthesis of N-(n-butylaminocarbonyl)-3-chloro-1-methyl-4-(5-methyl-5H,6H-1,4,2-dioxadin-3-yl) pyrazole-5-sulfonamide

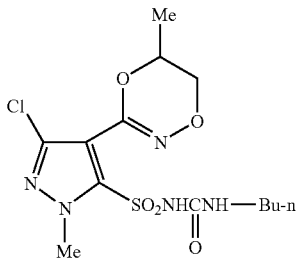

In a solution of 3-chloro-1-methyl-4-(5-methyl-5H,6H-1,4,2-dioxadin-3-yl)pyrazole-5-sulfonamide (5.31 g, 18.0 mmol) In 1,2-dichloroethane (30 ml), anhydrous potassium carbonate (3.76 g, 27.0 mmol) and n-butylisocyanate (2.14 g, 21.6 mmol) were added, and refluxed under heating for 1 hour. After cooling to room temperature, water (25 ml) was added, and stirred vigorously. The organic phase was separated, the resulting aqueous phase was adjusted to pH 1 by adding 35% hydrochloric acid, and extracted with 1,2-dichloroethane. The resulting 1,2-dichloroethane solution was washed with water, dried over anhydrous sodium sulfate, and the solvent was distilled off. A small amount of diisopropyl ether was added in the resulting residue, precipitated solid was filtered off, washed with water, dried to obtain the aimed product (3.53 g). Melting point 130-133° C. Proton nuclear magnetic resonance chemical shift values δ (ppm) (in CDCl$_3$) 0.89 (t, J=7.2 Hz, 3H), 1.20-1.50 (m, 7H), 3.10-3.19 (m, 2H), 3.36-3.83 (m, 1H), 4.16 (s, 3H), 4.15-4.29 (m, 1H), 4.56-4.67 (m, 1H), 6.56 (t, 1H), 9.50-9.92 (brs, 1H).

(2) Synthesis of 3-chloro-1-methyl-4-(5-methyl-5H, 6H-1,4,2-dioxadin-3-yl)pyrazole-5-sulfonyl isocyanate

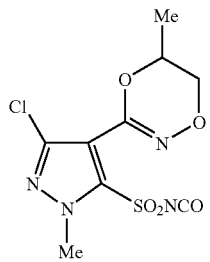

In toluene (15 ml), N-(n-butylaminocarbonyl)-3-chloro-1-methyl-4-(5-methyl-5H,6H-1,4,2-dioxadin-3-yl)pyrazol-5-sulfonamide (5.0 g, 13 mmol), bistrichloromethyl carbonate (9.4 g, 32 mmol) and triethylamine (0.1 ml) were added, and refluxed under heating for 8 hours. The solvent was distilled off to obtain the aimed product (4.0 g). Oily substance.

Referential Example 14

(1) Synthesis of bis(3-chloro-1-methyl-4-(5-methyl-5H,6H-1,4,2-dioxadin-3-yl)pyrazol-5-yl)disulfide

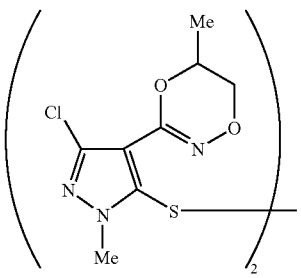

In a solution of 3-chloro-5-mercapto-1-methyl-4-(5-methyl-5H,6H-1,4,2-dioxadin-3-yl)pyrazole (1.0 g, 4.0 mmol) in N,N-dimethylformamide (10 ml), air was blown with stirring at room temperature over 3.5 hours. Precipitated solid was filtered off, washed with water and dried to obtain the aimed product (0.49 g). Melting point 165-167° C. Proton nuclear magnetic resonance chemical shut values δ (ppm) (in CDCl$_3$) 1.36 (d, J=6.3 Hz, 3H), 3.49-3.64 (m, 1H), 3.89 (s, 3H), 4.04-4.18 (m, 1H), 4.32-4.48 (m, 1H).

(2) Synthesis of 3-chloro-1-methyl-4-(5-methyl-5H, 6H-1,4,2-dioxadin-3-yl) pyrazole-5-yl)sulfonyl chloride (second version)

In a solution of bis(3-chloro-1-methyl (5-methyl-5H,8H-1,4,2-dioxadin-3-yl)pyrazol-5-yl)disulfide (2.5 g, 5.1 mmol) in 1,2-dichloroethane (50 ml), water (20 ml) was added, and under ice cooling, chlorine (2.1 g, 30 mmol) was introduced with vigorously stirring. In this process the temperature rised to 20° C. After excluding excess chlorine by introducing nitrogen, 1,2-dichloroethane phase was separated The resulting 1,2-dichloroethane solution was washed with saturated sodium hydrogen sulfite aqueous solution and water in that order, and then dried over anhydrous sodium sulfate, and the solvent was distilled off to obtain the aimed product (3.0 g). Melting point 63-68° C.

Referential Example 15

Synthesis of 3,5-dichloro-4-(5-iodomethyl-5H,6H-1,4,2-dioxadin-3-yl)-1-methylpyrazole (second version)

In a solution of N-allyloxy-3,5-dichloro-1-methylpyrazole-4-carboxylic acid amide (0.50 g, 2.0 mmol) in acetonitrile (5 ml), N-iodosuccinimide (0.67 g, 3.0 mmol) was added, and stirred at room temperature for 15 hours. Saturated sodium thiosulfite aqueous solution (10 ml) was added, extracted with ethyl acetate, the resulting ethyl acetate solution was washed with saturated sodium hydrogen carbonate, saturated sodium chloride aqueous solution and water in that order, dried over anhydrous sodium sulfate, and the solvent was distilled off. The resulting residue was purified with silica gel column chromatography (developing solution: n-hexane/ethyl acetate=3/1) to obtain the aimed product (0.60 g). Oily substance.

Referential Example 16

(1) Synthesis of 4-(5-bromomethyl-5H,6H-1,4,2-dioxadin-3-yl)-3,5-dichloro-1-methylpyrazole

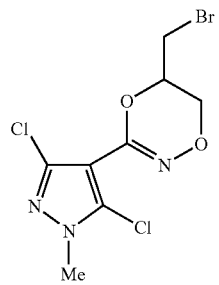

In a solution of N-allyloxy-3,5-dichloro-1-methylpyrazole-4-carboxylic acid amide (20.0 g, 80.0 mmol) in acetonitrile (200 ml), N-bromosuccinimide (17.1 g, 96.0 mmol) was added, and stirred at mom temperature for 1 hour. Saturated sodium thiosulfate aqueous solution (100 ml) was added, and acetonitrile was distilled off. Then, the mixture was extracted with ethyl acetate, the resulting ethyl acetate solution was washed with water and saturated sodium chloride aqueous solution in that order, dried over anhydrous sodium sulfate, and the solvent was distilled off. The resulting residue was purified with silica gel column chromatography (developing solution: n-hexane/ethyl acetate=3/1) to obtain the aimed product (18.4 g). Melting point 53-54° C. Proton nuclear magnetic resonance chemical shift values δ (ppm) (in CDCl$_3$) 3.57-3.61 (d, J=6.9 Hz, 2H), 3.83 (s, 3H), 4.06-4.11 (m, 1H), 4.29-4.33 (m, 1H), 4.65-4.72 (m, 1H).

(2) Synthesis of 3,5-dichloro-1-methyl-4-(5-methyl-5H,6H-1,4,2-dioxadin-3-yl)pyrazole (third version)

In a solution of 4-(5-bromomethyl-5H,6H-1,4,2-dioxadin-3-yl)-3,5-dichloro-1-methylpyrazole (0.50 g, 1.5 mmol) in N-methyl-2-pyrrolidone (5 ml), sodium boron hydride (0.11 g, 3.0 mmol) was added, and stirred at 60° C. for 1 hour. After cooling to room temperature, water (5 ml) was added, and adjusted to pH 1 by adding 35% hydrochloric acid, and extracted with ethyl acetate. The resulting ethyl acetate solution was washed with saturated sodium hydrogen carbonate, saturated sodium chloride aqueous solution and water in that order, dried over anhydrous sodium sulfate, and the solvent was distilled off. The resulting residue was purified with silica gel column chromatography (developing solution: n-hexane/ethyl acetate=5/2) to obtain the aimed product (0.31 g). Melting point 50-51° C.

Referential Example 17

(1) Synthesis of 5-benzylthio-1-methylpyrazole-4-carbohydroxamic acid

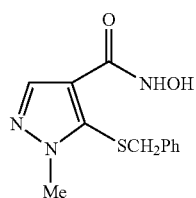

In a suspension of 5-benzylthio-1-methylpyrazole-4-carboxylic acid (15.9 g, 64.0 mmol) in toluene (100 ml), thionyl chloride (11.4 g, 95.8 mmol) and N,N-dimethylformamide (0.1 g) were added, and refluxed for 4 hours. The residue obtained by distilling off the solvent was dissolved in tetrahydrofuran (40 ml), On the other hand, in a solution of hydroxyamine hydrochloride (13.3 g, 191 mmol) in water (40 ml), a solution of 85% potassium hydroxide (12.6 g, 191 mmol) in water (40 ml) was added at 5-15° C., and stirred at room temperature for 15 minutes. Then, the above-mentioned tetrahydrofuran solution was added dropwise at 3-15° C. After further stirring at 3° C. for 1.5 hour, the mixture was adjusted to pH 3-4 by adding 35% hydrochloric acid (20 ml) and extracted with ethyl acetate. The resulting ethyl acetate solution was washed with water, dried over anhydrous sodium suite, and the solvent was distilled off. The resulting residue was purified with silica gel column chromatography (developing solution: n-hexane/ethyl acetate=1/1) to obtain the aimed product (10.3 g). Resinous substance. Proton nuclear magnetic resonance chemical shift values δ (ppm) (in CDCl$_3$) 3.42 (s, 3H), 3.95 (s, 2H), 6.93-7.01 (m, 2H), 7.20-7.28 (m, 3H), 8.04 (s, 1H), 9.76 (brs 1H).

(2) Synthesis of N-allyloxy-5-benzylthio-1-methylpyrazole-4-carboxylic acid amide

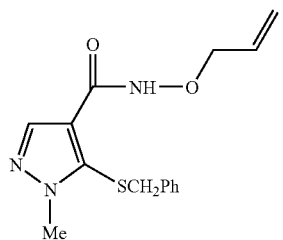

In a solution of potassium carbonate (1.3 g, 9.4 mmol) in water (10 ml), a solution of 5-benzylthio-1-methylpyrazole-4-carbohydroxamic acid (2.0 g, 7.6 mmol) and allyl bromide (1.1 g, 9.1 mmol) in toluene (10 ml) were added, and stirred at 50° C. for 4 hours. After cooling to room temperature, the mixture was adjusted to pH 1 by adding 35% hydrochloric acid and extracted with ethyl acetate. The resulting ethyl acetate solution was washed with water, dried over anhydrous sodium sulfate, and the solvent was distilled off to obtain the aimed product (1.9 g). Oily substance. Proton nuclear magnetic resonance chemical shift values δ (ppm) (in CDCl$_3$) 3.42 (s, 3H), 3.95 (s, 2H), 4.49 (d, J=6.3 Hz, 2H), 5.33-5.43 (m, 2H), 6.00-6.16 (m, 1H), 6.93-7.00 (m, 2H), 7.21-7.30 (m, 3H), 8.08 (s, 1H), 9.68 (brs, 1H).

(3) Synthesis of 5-benzylthio-4-(5-iodomethyl-5H,6H-1,4,2-dioxadin-3-yl)-1-methylpyrazole

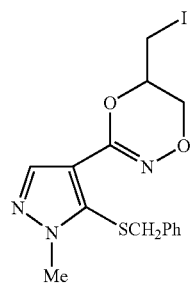

In a solution of N-allyloxy-5-benzylthio-1-methylpyrazole-4-carboxylic acid amide (1.8 g, 5.9 mmol) in acetonitrile (10 ml), iodine (4.5 g, 18 mmol) was added, and stirred at room temperature for 8 hours. Saturated sodium thiosulfate aqueous solution (30 ml) was added, extracted with ethyl acetate, the resulting ethyl acetate solution was washed with saturated sodium hydrogen carbonate, saturated sodium chloride aqueous solution and water in that order, dried over anhydrous sodium sulfate, and the solvent was distilled off. The resulting residue was purified with silica gel column chromatography (developing solution: n-hexane/ethyl acetate=3/1) to obtain the aimed product (1.7 g). Resinous substance. Proton nuclear magnetic resonance chemical shift values δ (ppm) (in CDCl$_3$) 3.36-3.42 (m, 5H), 3.98-4.05 (m, 3H), 4.31-4.38 (m, 1H), 4.54-4.59 (m, 1H), 6.97-7.02 (m, 2H), 7.20-7.24 (m, 3H), 7.79 (s, 1H).

(4) Synthesis of 5-benzylthio-1-methyl-4-(5-methyl-5H,6H-1,4,2-dioxadin-3-yl)pyrazole

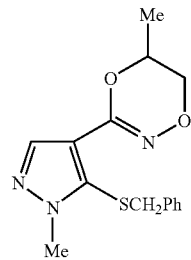

In a solution of 5-benzylthio-4-(5-iodomethyl-5H,6H-1,4,2-dioxadin-3-yl)-1-methylpyrazole (1.6 g, 3.7 mmol) in N,N-dimethylformamide (8 ml), a solution of sodium boron hydride (0.21 g, 5.6 mmol) in N,N-dimethylformamide (5 ml) was added dropwise over 0.3 hour, and further stirred at 50° C. for 1 hour. After cooling to room temperature, water (20 ml) was added, and the mixture was adjusted to pH 1 by adding 35% hydrochloric acid, and extracted with ethyl acetate. The resulting ethyl acetate solution was washed with 6% hydrochloric acid and water in that order, dried over anhydrous sodium sulfate and the solvent was distilled off to obtain the desired product (1.1 g). Resinous substance. Proton nuclear magnetic resonance chemical shift values δ (ppm) (an CDCl$_3$) 1.43 (d, J=6.3 Hz, 3H), 3.36 (s, 3H), 3.69-3.77 (m, 1H), 4.04 (q, J=12.6 Hz, 2H), 4.21-4.27 (m, 1H), 4.55-4.61 (m, 1H), 6.98-7.03 (m, 2H), 7.19-7.24 (m, 3H), 7.76 (s, 1H).

(5) Synthesis of 1-methyl-4-(5-methyl-5H,6H-1,4,2-dioxadin-3-yl)pyrazole-5-sulfonamide

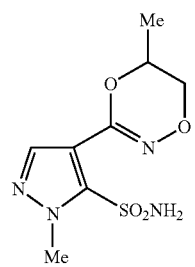

In a solution of 5-benzylthio-1-methyl-4-(5-methyl-5H,6H-1,4,2-dioxadin-3-yl)pyrazole (1.1 g, 3.5 mmol) in 1,2-dichloroethane (10 ml), water (10 ml) and 35% hydrochloric acid (0.1 g) were added, and chlorine (2.5 g, 35 mmol was introduced at 5° C. with vigorously stirring in this process, the reaction solution generated heat to 19° C. After excluding excess chlorine by introducing nitrogen, water (20 ml) was added, and extracted with 1,2-dichloroethane. The resulting 1,2-dichloroethane was concentrated to 8 ml under reduced pressure. This solution was added dropwise in a separately prepared solution of 1,2-dichloroethane (8 ml) in which 28% ammonia water was added at 5° C. with vigorously stirring, and further stirred for 0.5 hour The resulting solution was adjusted to pH 1 by adding 35% hydrochloric acid, and extracted with 1,2-dichloroethane. The resulting 1,2-dichloroethane solution was dried over anhydrous sodium sulfate and the residue obtained by distilling off the solvent was recrystallized from toluene to obtain the desired product (0.43 g). Melting point 97-99° C. Proton nuclear magnetic resonance chemical shift values δ (ppm) (in CDCl$_3$) 1.43 (d, J=6.3 Hz, 3H), 3.70-3.77 (m, 1H), 4.19-4.26 (m, 4H), 4.55-4.62 (m, 1H), 6.49 (brs, 2M), 7.75 (s, 1H).

Referential Example 18

Synthesis of 4-(5-methyl-5H,6H-1,4,2-dioxadin-3-yl)-1-(pyridin-2-yl)pyrazole-5-sulfonamide

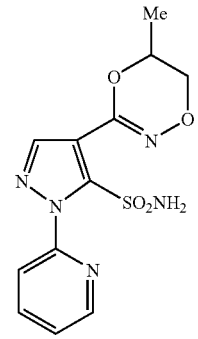

The procedure similar to that of Referential Example 1 was carried by using 5-benzylthio-1-(pyridin-2-yl)pyrazol-4-carboxylic acid chloride (3.63 g, 11.0 mmol) as a starting material to obtain the aimed product (0.45 g). Resinous substance. Proton nuclear magnetic resonance chemical shift values δ (ppm) (in CDCl$_3$) 1.43 (d, J=6.3 Hz, 3H), 3.77-3.83 (m, 1H), 4.22-4.26 (m, 1H), 4.58-4.63 (m, 1H), 6.41 (brs, 2H), 7.42-7.44 (m, 1H), 7.78-7.80 (m, 1H), 7.87 (s, 1H), 7.93-7.98 (m, 1H), 8.48-8.50 (m, 1H).

Table 1 shows the structural formulae and physical properties of the compounds synthesized by using the procedure similar to that of Examples and Referential Examples mentioned above together with the compounds described in Examples and Referential Examples mentioned above.

TABLE 1

[Structure: pyrazole-dioxazine with SO2NHC(O)NH linked to pyrimidine/triazine bearing X, Y, Z]

| No. | R¹ | R² | R³ | R⁴ | R⁵ | R⁶ | X | Y | Z | Physical properties (Melting point ° C.) |
|---|---|---|---|---|---|---|---|---|---|---|
| 1 | Me | Cl | Me | H | H | H | MeO | MeO | CH | 177-179 |
| 2 | Me | Cl | ICH₂ | H | H | H | MeO | MeO | CH | 91-94 |
| 3 | Me | Cl | Me | Me | H | H | MeO | MeO | CH | 189-191 |
| 4 | Me | Cl | Me | ICH₂ | H | H | MeO | MeO | CH | 90-93 |
| 5 | Me | Me | Me | H | H | H | MeO | MeO | CH | 180-182 |
| 6 | Me | Me | ICH₂ | H | H | H | MeO | MeO | CH | 66-69 |
| 7 | Me | Me | Me | Me | H | H | MeO | MeO | CH | 199-201 |
| 8 | Me | Me | Me | ICH₂ | H | H | MeO | MeO | CH | 133-135 |
| 9 | Me | Me | H | H | Me | H | MeO | MeO | CH | 187-189 |
| 10 | Me | H | Me | H | H | H | MeO | MeO | CH | 154-157 |
| 11 | Me | Cl | Me | H | H | H | MeO | Me | CH | 181-182 |
| 12 | Me | Cl | Me | H | H | H | Me | Me | CH | 176-177 |
| 13 | Me | Cl | Me | H | H | H | MeO | MeO | N | 150-151 |
| 14 | Me | Cl | Me | H | H | H | MeO | Me | N | 191-193 |
| 15 | Me | Cl | Me | H | H | H | Me | Me | N | |
| 16 | Me | Cl | Et | H | H | H | MeO | MeO | CH | |
| 17 | Me | Me | Et | H | H | H | MeO | MeO | CH | |
| 18 | Me | H | Et | H | H | H | MeO | MeO | CH | |
| 19 | 2-Py | H | Me | H | H | H | MeO | MeO | CH | 100-101 |
| 20 | Me | Cl | Me | H | H | H | MeO | Cl | CH | 157-158 |

Next, examples of the compounds included in the present invention are in Table 2 together with the compounds synthesized in Examples mentioned above. However, the present invention is not limited thereto. In the meantime, the symbols in the table are as defined above.

TABLE 2

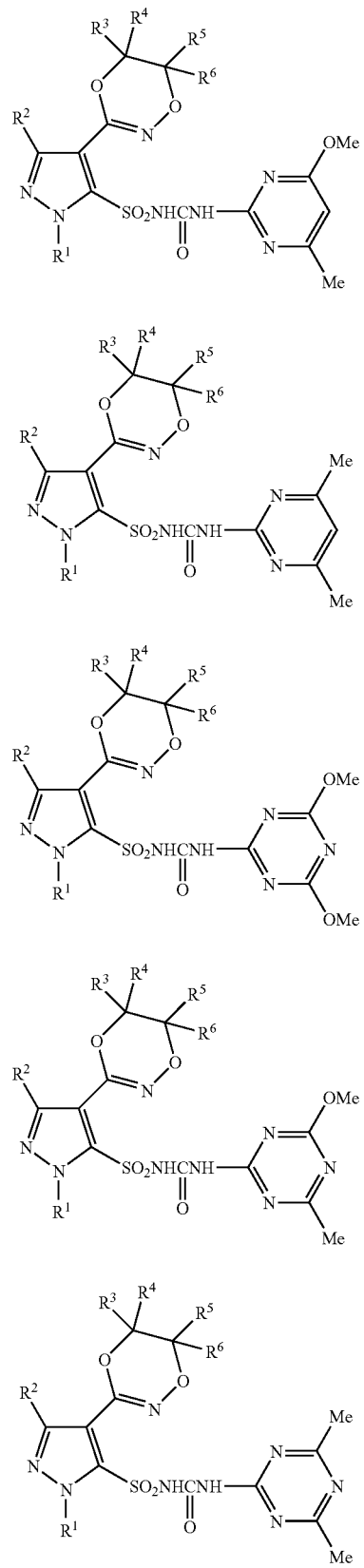

TABLE 2-continued

TABLE 2-continued

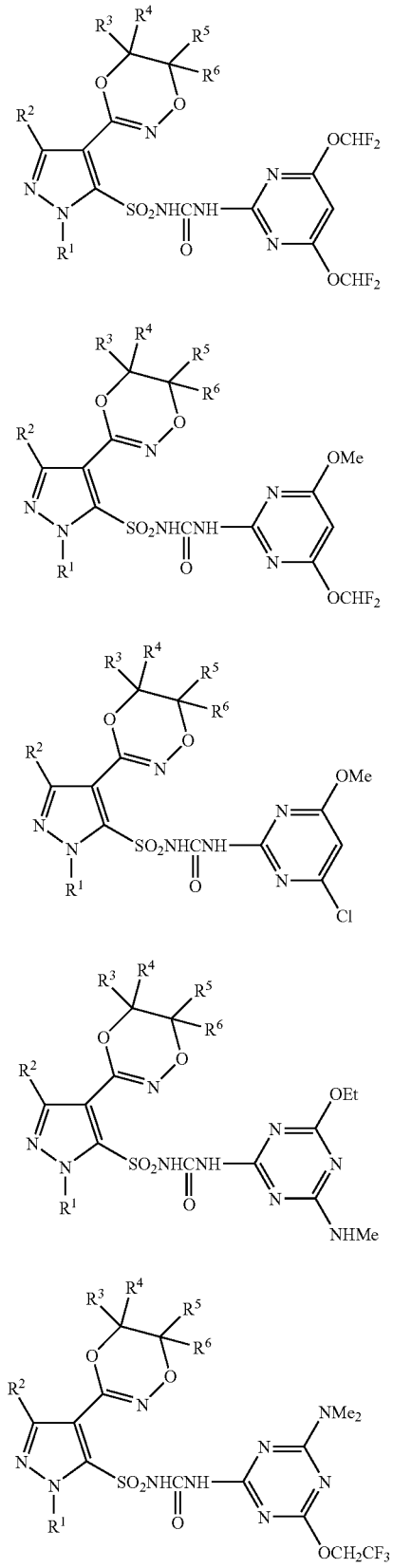

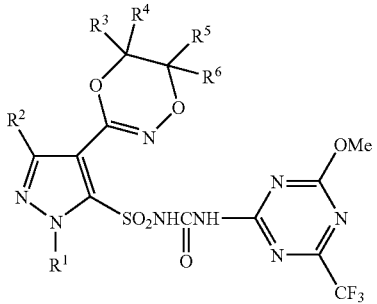

| R¹ | R² | R³ | R⁴ | R⁵ | R⁶ |
|---|---|---|---|---|---|
| Me | H | Me | H | H | H |
| Me | H | H | H | Me | H |
| Me | H | Me | Me | H | H |
| Me | H | Me | H | Me | H |
| Me | H | H | H | Me | Me |
| Me | H | Me | Me | Me | H |
| Me | H | Me | H | Me | Me |
| Me | H | Me | Me | Me | Me |
| Me | H | CH₂I | H | H | H |
| Me | H | CH₂I | Me | H | H |
| Et | H | Me | H | H | H |
| Et | H | H | H | Me | H |
| Et | H | Me | Me | H | H |
| Et | H | Me | H | Me | H |
| Et | H | H | H | Me | Me |
| Et | H | Me | Me | Me | H |
| Et | H | Me | H | Me | Me |
| Et | H | Me | Me | Me | Me |
| Et | H | CH₂I | H | H | H |
| Et | H | CH₂I | Me | H | H |
| CH₂OMe | H | Me | H | H | H |
| CH₂OMe | H | H | H | Me | H |
| CH₂OMe | H | Me | Me | H | H |
| CH₂OMe | H | Me | H | Me | H |
| CH₂OMe | H | H | H | Me | Me |
| CH₂OMe | H | Me | Me | Me | H |
| CH₂OMe | H | Me | H | Me | Me |
| CH₂OMe | H | Me | Me | Me | Me |
| CH₂OMe | H | CH₂I | H | H | H |
| CH₂OMe | H | CH₂I | Me | H | H |
| Ph | H | Me | H | H | H |
| Ph | H | H | H | Me | H |
| Ph | H | Me | Me | H | H |
| Ph | H | Me | H | Me | H |
| Ph | H | H | H | Me | Me |
| Ph | H | Me | Me | Me | H |
| Ph | H | Me | H | Me | Me |
| Ph | H | Me | Me | Me | Me |
| Ph | H | CH₂I | H | H | H |
| Ph | H | CH₂I | Me | H | H |
| 2-Py | H | Me | H | H | H |
| 2-Py | H | H | H | Me | H |
| 2-Py | H | Me | Me | H | H |
| 2-Py | H | Me | H | Me | H |
| 2-Py | H | H | H | Me | Me |
| 2-Py | H | Me | Me | Me | H |
| 2-Py | H | Me | H | Me | Me |
| 2-Py | H | Me | Me | Me | Me |
| 2-Py | H | CH₂I | H | H | H |
| 2-Py | H | CH₂I | Me | H | H |
| Me | Me | Me | H | H | H |
| Me | Me | H | H | Me | H |
| Me | Me | Me | Me | H | H |
| Me | Me | Me | H | Me | H |
| Me | Me | H | H | Me | Me |
| Me | Me | Me | Me | Me | H |
| Me | Me | Me | H | Me | Me |
| Me | Me | Me | Me | Me | Me |
| Me | Me | CH₂I | H | H | H |
| Me | Me | CH₂I | Me | H | H |
| Et | Me | Me | H | H | H |

TABLE 2-continued

| | | | | | |
|---|---|---|---|---|---|
| Et | Me | H | H | Me | H |
| Et | Me | Me | Me | H | H |
| Et | Me | Me | H | Me | H |
| Et | Me | H | H | Me | Me |
| Et | Me | Me | Me | Me | H |
| Et | Me | Me | H | Me | Me |
| Et | Me | Me | Me | Me | Me |
| Et | Me | CH$_2$I | H | H | H |
| Et | Me | CH$_2$I | Me | H | H |
| CH$_2$OMe | Me | Me | H | H | H |
| CH$_2$OMe | Me | H | H | Me | H |
| CH$_2$OMe | Me | Me | Me | H | H |
| CH$_2$OMe | Me | Me | H | Me | H |
| CH$_2$OMe | Me | H | H | Me | Me |
| CH$_2$OMe | Me | Me | Me | Me | H |
| CH$_2$OMe | Me | Me | H | Me | Me |
| CH$_2$OMe | Me | Me | Me | Me | Me |
| CH$_2$OMe | Me | CH$_2$I | H | H | H |
| CH$_2$OMe | Me | CH$_2$I | Me | H | H |
| Ph | Me | Me | H | H | H |
| Ph | Me | H | H | Me | H |
| Ph | Me | Me | Me | H | H |
| Ph | Me | Me | H | Me | H |
| Ph | Me | H | H | Me | Me |
| Ph | Me | Me | Me | Me | H |
| Ph | Me | Me | H | Me | Me |
| Ph | Me | Me | Me | Me | Me |
| Ph | Me | CH$_2$I | H | H | H |
| Ph | Me | CH$_2$I | Me | H | H |
| 2-Py | Me | Me | H | H | H |
| 2-Py | Me | H | H | Me | H |
| 2-Py | Me | Me | Me | H | H |
| 2-Py | Me | Me | H | Me | H |
| 2-Py | Me | H | H | Me | Me |
| 2-Py | Me | Me | Me | Me | H |
| 2-Py | Me | Me | H | Me | Me |
| 2-Py | Me | Me | Me | Me | Me |
| 2-Py | Me | CH$_2$I | H | H | H |
| 2-Py | Me | CH$_2$I | Me | H | H |
| Me | Cl | Me | H | H | H |
| Me | Cl | H | H | Me | H |
| Me | Cl | Me | Me | H | H |
| Me | Cl | Me | H | Me | H |
| Me | Cl | H | H | Me | Me |
| Me | Cl | Me | Me | Me | H |
| Me | Cl | Me | H | Me | Me |
| Me | Cl | Me | Me | Me | Me |
| Me | Cl | CH$_2$I | H | H | H |
| Me | Cl | CH$_2$I | Me | H | H |
| Et | Cl | Me | H | H | H |
| Et | Cl | H | H | Me | H |
| Et | Cl | Me | Me | H | H |
| Et | Cl | Me | H | Me | H |
| Et | Cl | H | H | Me | Me |
| Et | Cl | Me | Me | Me | H |
| Et | Cl | Me | H | Me | Me |
| Et | Cl | Me | Me | Me | Me |
| Et | Cl | CH$_2$I | H | H | H |
| Et | Cl | CH$_2$I | Me | H | H |
| CH$_2$OMe | Cl | Me | H | H | H |
| CH$_2$OMe | Cl | H | H | Me | H |
| CH$_2$OMe | Cl | Me | Me | H | H |
| CH$_2$OMe | Cl | Me | H | Me | H |
| CH$_2$OMe | Cl | H | H | Me | Me |
| CH$_2$OMe | Cl | Me | Me | Me | H |
| CH$_2$OMe | Cl | Me | H | Me | Me |
| CH$_2$OMe | Cl | Me | Me | Me | Me |
| CH$_2$OMe | Cl | CH$_2$I | H | H | H |
| CH$_2$OMe | Cl | CH$_2$I | Me | H | H |
| Ph | Cl | Me | H | H | H |
| Ph | Cl | H | H | Me | H |
| Ph | Cl | Me | Me | H | H |
| Ph | Cl | Me | H | Me | H |
| Ph | Cl | H | H | Me | Me |
| Ph | Cl | Me | Me | Me | H |
| Ph | Cl | Me | H | Me | Me |
| Ph | Cl | Me | Me | Me | Me |
| Ph | Cl | CH$_2$I | H | H | H |
| Ph | Cl | CH$_2$I | Me | H | H |
| 2-Py | Cl | Me | H | H | H |
| 2-Py | Cl | H | H | Me | H |
| 2-Py | Cl | Me | Me | H | H |
| 2-Py | Cl | Me | H | Me | H |
| 2-Py | Cl | H | H | Me | Me |
| 2-Py | Cl | Me | Me | Me | H |
| 2-Py | Cl | Me | H | Me | Me |
| 2-Py | Cl | Me | Me | Me | Me |
| 2-Py | Cl | CH$_2$I | H | H | H |
| 2-Py | Cl | CH$_2$I | Me | H | H |
| Me | Br | Me | H | H | H |
| Me | Br | H | H | Me | H |
| Me | Br | Me | Me | H | H |
| Me | Br | Me | H | Me | H |
| Me | Br | H | H | Me | Me |
| Me | Br | Me | Me | Me | H |
| Me | Br | Me | H | Me | Me |
| Me | Br | Me | Me | Me | Me |
| Me | Br | CH$_2$I | H | H | H |
| Me | Br | CH$_2$I | Me | H | H |
| Et | Br | Me | H | H | H |
| Et | Br | H | H | Me | H |
| Et | Br | Me | Me | H | H |
| Et | Br | Me | H | Me | H |
| Et | Br | H | H | Me | Me |
| Et | Br | Me | Me | Me | H |
| Et | Br | Me | H | Me | Me |
| Et | Br | Me | Me | Me | Me |
| Et | Br | CH$_2$I | H | H | H |
| Et | Br | CH$_2$I | Me | H | H |
| CH$_2$OMe | Br | Me | H | H | H |
| CH$_2$OMe | Br | H | H | Me | H |
| CH$_2$OMe | Br | Me | Me | H | H |
| CH$_2$OMe | Br | Me | H | Me | H |
| CH$_2$OMe | Br | H | H | Me | Me |
| CH$_2$OMe | Br | Me | Me | Me | H |
| CH$_2$OMe | Br | Me | H | Me | Me |
| CH$_2$OMe | Br | Me | Me | Me | Me |
| CH$_2$OMe | Br | CH$_2$I | H | H | H |
| CH$_2$OMe | Br | CH$_2$I | Me | H | H |
| Ph | Br | Me | H | H | H |
| Ph | Br | H | H | Me | H |
| Ph | Br | Me | Me | H | H |
| Ph | Br | Me | H | Me | H |
| Ph | Br | H | H | Me | Me |
| Ph | Br | Me | Me | Me | H |
| Ph | Br | Me | H | Me | Me |
| Ph | Br | Me | Me | Me | Me |
| Ph | Br | CH$_2$I | H | H | H |
| Ph | Br | CH$_2$I | Me | H | H |
| 2-Py | Br | Me | H | H | H |
| 2-Py | Br | H | H | Me | H |
| 2-Py | Br | Me | Me | H | H |
| 2-Py | Br | Me | H | Me | H |
| 2-Py | Br | H | H | Me | Me |
| 2-Py | Br | Me | Me | Me | H |
| 2-Py | Br | Me | H | Me | Me |
| 2-Py | Br | Me | Me | Me | Me |
| 2-Py | Br | CH$_2$I | H | H | H |
| 2-Py | Br | CH$_2$I | Me | H | H |
| Me | OMe | Me | H | H | H |
| Me | OMe | H | H | Me | H |
| Me | OMe | Me | Me | H | H |
| Me | OMe | Me | H | Me | H |
| Me | OMe | H | H | Me | Me |
| Me | OMe | Me | Me | Me | H |
| Me | OMe | Me | H | Me | Me |
| Me | OMe | Me | Me | Me | Me |
| Me | OMe | CH$_2$I | H | H | H |
| Me | OMe | CH$_2$I | Me | H | H |
| Et | OMe | Me | H | H | H |
| Et | OMe | H | H | Me | H |
| Et | OMe | Me | Me | H | H |
| Et | OMe | Me | H | Me | H |
| Et | OMe | H | H | Me | Me |
| Et | OMe | Me | Me | Me | H |
| Et | OMe | Me | H | Me | Me |
| Et | OMe | Me | Me | Me | Me |
| Et | OMe | CH$_2$I | H | H | H |

TABLE 2-continued

| | | | | | |
|---|---|---|---|---|---|
| Et | OMe | CH$_2$I | Me | H | H |
| CH$_2$OMe | OMe | Me | H | H | H |
| CH$_2$OMe | OMe | H | H | Me | H |
| CH$_2$OMe | OMe | Me | Me | H | H |
| CH$_2$OMe | OMe | Me | H | Me | H |
| CH$_2$OMe | OMe | H | H | Me | Me |
| CH$_2$OMe | OMe | Me | Me | Me | H |
| CH$_2$OMe | OMe | Me | H | Me | Me |
| CH$_2$OMe | OMe | Me | Me | Me | Me |
| CH$_2$OMe | OMe | CH$_2$-I | H | H | H |
| CH$_2$OMe | OMe | CH$_2$-I | Me | H | H |
| Ph | OMe | Me | H | H | H |
| Ph | OMe | H | H | Me | H |
| Ph | OMe | Me | Me | H | H |
| Ph | OMe | Me | H | Me | H |
| Ph | OMe | H | H | Me | Me |
| Ph | OMe | Me | Me | Me | H |
| Ph | OMe | Me | H | Me | Me |
| Ph | OMe | Me | Me | Me | Me |
| Ph | OMe | CH$_2$I | H | H | H |
| Ph | OMe | CH$_2$I | Me | H | H |
| 2-Py | OMe | Me | H | H | H |
| 2-Py | OMe | H | H | Me | H |
| 2-Py | OMe | Me | Me | H | H |
| 2-Py | OMe | Me | H | Me | H |
| 2-Py | OMe | H | H | Me | Me |
| 2-Py | OMe | Me | Me | Me | H |
| 2-Py | OMe | Me | H | Me | Me |
| 2-Py | OMe | Me | Me | Me | Me |
| 2-Py | OMe | CH$_2$I | H | H | H |
| 2-Py | OMe | CH$_2$I | Me | H | H |
| Me | H | Et | H | H | H |
| Me | Me | Et | H | H | H |
| Me | Cl | Et | H | H | H |
| Me | Br | Et | H | H | H |
| Me | OMe | Et | H | H | H |
| Et | H | Et | H | H | H |
| Et | Me | Et | H | H | H |
| Et | Cl | Et | H | H | H |
| Et | Br | Et | H | H | H |
| Et | OMe | Et | H | H | H |
| CH$_2$OMe | H | Et | H | H | H |
| CH$_2$OMe | Me | Et | H | H | H |
| CH$_2$OMe | Cl | Et | H | H | H |
| CH$_2$OMe | Br | Et | H | H | H |
| CH$_2$OMe | OMe | Et | H | H | H |
| Ph | H | Et | H | H | H |
| Ph | Me | Et | H | H | H |
| Ph | Cl | Et | H | H | H |
| Ph | Br | Et | H | H | H |
| Ph | OMe | Et | H | H | H |
| 2-Py | H | Et | H | H | H |
| 2-Py | Me | Et | H | H | H |
| 2-Py | Cl | Et | H | H | H |
| 2-Py | Br | Et | H | H | H |
| 2-Py | OMe | Et | H | H | H |

Although the application dosage of the compound of the present invention as herbicide is varied depending on the applied scene, the applied season, applied method, weed to be prevented and cultivated crop, etc., generally it is about 0.001 to 50 kg, preferably about 0.01 to 10 kg of the active component per hectare (ha). The compound of the present invention can be use for either submerged soil treatment or foliage treatment as herbicide for paddy. The woods of paddy include for example weeds of Potamogetonaceae represented by *Potamogeton disinctus*, etc., weeds of Alismataceae represented by *Alisma canaliculatum, Sagittaria pygmaea* and, *Sagttaria trifolla*, etc., weds of Gramineae represented by *Leptochloa chinensis, Echinochloa crus-galli* and *Echinochloa oryzicola*, etc., weeds of Cyperaceae represented by *Eiocharis kuroguwai, Scirpus juncoides, Scripus nipponicus, Cyperus serotinus* and *Cyperus difformis*, etc., weeds of Lemnaceae represented by *Spirodela polyrhiza* and *Lemna paucicostata*, etc., weeds of Commelinaceae represented by *Murdannia keisak*, etc., weeds of Pontederiaceae presented by *Monochoria korsakowii* and *Monochoriavaginalis*, etc., weeds of Elatinaceae represented by *Elatine triandra*, etc., weeds of Lythraceae represented by *Ammannia multiflora* and *Rotala indica*, etc., weeds of Oenotheraceae represented by *Lidwigla epiloblodes*, etc., weeds of Scrophulariaceae represented by *Dopatrium junceum, Lindemia pyxidaria* and *Lindemia dubia*, etc., and weeds of Composite represented by *Bidens frondosa* and *Bidens tripartita*, etc., or the like.

In addition, the compound of the present invention can be used for any treatment processes of soil treatment, soil Incorporation treatment and foliage treatment as herbicide for dry field. It can be applied for preventing several weeds on not only agricultural and horticultural area such as paddy, dry field and orchard, etc., but also non-crop lands such as playing field, vacant space and sides of rail track, etc. The compound of the present invention may be applied together with other kinds of herbicides, various kinds of insecticides, fungicides, vegetable growth regulators or synergists, and the like when it formulated or sprayed if necessary.

Particularly, the combined application with other herbicides can lead to low cost due to decrease in applied herbicide amount, enlargement of herbicidal spectrum due to synergistic effect, and higher herbicidal effect. Further, the compound of the present invention can be combined with plural known herbicide simultaneously.

Preferable herbicides used in a combination with the compound of the present invention include for example pyrazosulfuron-ethyl (generic name), bensulfuron-methyl (generic name), cinosulfuron (generic name), imazosulfuron (generic name), azimsulfuron (generic name), halosulfuron-methyl (generic name), pretilachlor (generic name), esprocarb (generic name), pyrazolate (generic name), pyrazoxyfen (generic name), benzofenap (generic name), daimuron (generic name), bromobutide (generic name), naproanilide (generic name), clomeprop (generic name), CNP (generic name), chlomethoxynil (generic name), bifenox (generic name), oxadiazon (generic name), oxadiargyl (generic name), cafenstrole (generic name), oxaziclomefone (generic name), indanofan (generic name), pentoxazone (generic name), pyriminobac-methyl (generic name), cyhalofop-butyl (generic name), fentrazamide (generic name), mefenacet (generic name), butachlor (generic name), butenachlor (generic name), dithiopyl (generic name), benfuresate (generic name), pyributicarb (generic name), benthiocarb (generic name), dimepiperate (generic name), molinate (generic name), butamifos (generic name), quinclorec (generic name), cinmethylin (generic name), simetryn (generic name), bensulide (generic name), dimethametryn (generic name), MCPA, MCPB, etobenzanid, cumyluron (generic name), thenylchlor (generic name), ethoxysulfuron (generic name), quinoclamine (generic name), benzobicyclon (generic name), pyriftalid (generic name), bispyribac, HAS-961 (test name), anilofos (generic name), OK-701 (test name), cyclosulfamuron (generic name), DASH-001 (test name), AVH-301 (test name), KUH-021 (test name) and TH-547 (test name), etc.

When the compound of the present invention is applied as a herbicide, it can be practically provided in an arbitrary formulation form such as liquid formulations, emulsifiable concentrate, wettable powders, dry flowables, flowables, dust formulations or granules, etc. generally by mixing with a suitable solid carrier or liquid carrier, optionally along with surfactant, penetrating agent, spreading agent, thickner, antifreezing agent, binder, anti-caking agent or disintegrating agent, etc.

In addition, from the viewpoint of an elimination or reduction of labor and an improvement of safety, the formulations in any desired forms described above may be included into a water-soluble bag.

The solid carrier includes, for example, natural minerals such as kaolinite, pyrofilite, celicite, talc, bentonite, acid china clay, attapulgite, zeolite and diatomaceous earth, etc., inorganic salts such as calcium carbonate, ammonium sulfate, sodium sulfate and potassium chloride, etc., synthetic silica, and synthetic silicate, and the like.

The liquid carrier includes for example water, alcohols (ethylene glycol, propylene glycol, isopropanol, etc.), aromatic hydrocarbons (xylene, alkylbenzene, alkylnaphthalene, etc.) ethers (propyl cellosolve, etc.), ketones (cyclohexanone, etc.), esters (γ-butyrolactone, etc.), acid amides (N-methylpyrrolidone, N-octylpyrrolidone, etc.), and vegetable oils (soybean oil, rapeseed oil, cottonseed oil, caster oil, etc.), and the like.

These solid and liquid carriers may be used alone or in combination of two or more kinds in combination.

As the surfactant, there may be mentioned, for example, nonionic surfactants such as polyoxyethylene alkyl aryl ether, polyoxyethylene styryl phenyl ether, polyoxyethylene polyoxypropylene block copolymer, polyoxyethylene fatty acid ester, sorbitan acid ester, and polyoxyethylene sorbitan fatty acid ester, etc., as well as ionic surfactants such as alkylbenzenesulfonate, lignine sulfonate, alkylsulfosuccinate, naphthalene sulfonate, alkylnaphthalene sulfonate, formalin condensate salt of naphthalene sulfonic acid, formalin condensate salt of alkylnaphthalene sulfonic acid, polyoxyethylene alkyl aryl ether sulfate or phosphate, polyoxyethylene styryl phenyl ether sulfate or phosphate, alkylamine salt, etc.

A content of these surfactants is not specifically limited, and it is desirably in the range of 0.05 to 20 parts by weight in general based on 100 parts by weight of the preparation according to the present invention. Also, these surfactants may be used alone or in combination of two or more kinds in combination.

Next, formulation examples of the preparation in case where the compound of the present invention is used are shown below. Provided that formulation examples of the present invention am not limited only thereto. In the interim, in the following Formulation Examples, "part(s)" mean part(s) by weight.

Wettable Powder

| | |
|---|---|
| Compound of the present invention | 0.1 to 80 parts |
| Solid carrier | 5 to 98.9 parts |
| Surfactant | 1 to 10 parts |
| Others | 0 to 5 parts |

As other components, there may be mentioned, for example, a non-caking agent, a decomposition preventing agent, and the like.

Emulsifiable Concentrate

| | |
|---|---|
| Compound of the present invention | 0.1 to 30 parts |
| Liquid carrier | 55 to 95 parts |
| Surfactant | 4.9 to 15 parts |

Flowable

| | |
|---|---|
| Compound of the present invention | 0.1 to 70 parts |
| Liquid carrier | 15 to 98.89 parts |
| Surfactant | 1 to 12 parts |
| Other components | 0.01 to 30 parts |

As other components, there may be mentioned, for example, an antifreezing agent, a thickening agent, and the like.

Dry Flowable

| | |
|---|---|
| Compound of the present invention | 0.1 to 90 parts |
| Solid carrier | 0 to 98.9 parts |
| Surfactant | 1 to 20 parts |
| Other components | 0 to 10 parts |

As other components, there may be mentioned, for example, a binder, a decomposition preventing agent, and the like.

Liquid Formulation

| | |
|---|---|
| Compound of the present invention | 0.01 to 30 parts |
| Liquid carrier | 0.1 to 50 parts |
| Water | 50 to 99.89 parts |
| Other components | 0 to 10 parts |

As other components, there may be mentioned, for example, an antifreezing agent, a spreading agent, and the like.

Granule

| | |
|---|---|
| Compound of the present invention | 0.01 to 10 parts |
| Solid carrier | 90 to 99.99 parts |
| Other components | 0 to 10 parts |

As other components, there may be mentioned, for example, a binder, a decomposition preventing agent, and the like.

The above-mentioned formulation is sprayed as such or in a form diluted with water by 1- to 10000-fold.

Formulation Examples

Next, agrochemical-formulation examples using the compound of the present invention as an active component are concretely described, but the present invention is not limited thereto. In the interim, in the following Formulation Examples, "part(s)" mean part(s) by weight.

Formulation Example 1

Wettable Powder

| | |
|---|---|
| Compound of the present invention No. 1 | 20 parts |
| Pyrophylite | 76 parts |
| Solpol 5039 | 2 parts |
| (A mixture of a nonionic surfactant and an anionic surfactant: available from TOHO Chemical Industry Co., LTD, Trade-name) | |
| CARPREX #80D | 2 parts |
| (Synthetic hydrated silicic acid: available from Shionogi & Co., Ltd., Tradename) | |

The above materials are uniformly mixed and pulverized to make wettable powder.

Formulation Example 2

Emulsifiable Concentrate

| | |
|---|---|
| Compound of the present invention No. 1 | 5 parts |
| Xylene | 75 parts |
| N-methylpyrrolidone | 15 parts |
| Solpol 2680 | 5 parts |
| (A mixture of a nonionic surfactant and an anionic surfactant available from TOHO Chemical Industry Co., LTD, Trade-name) | |

The above materials are uniformly mixed to make emulsifiable concentrate.

Formulation Example 3

Flowable

| | |
|---|---|
| Compound of the present invention No. 1 | 25 parts |
| Agrisol S-710 | 10 parts |
| (a nonionic surfactant available from KAO CORPORATION, Trade-name) | |
| Lunox 1000C | 0.5 part |
| (an anionic surfactant: available from TOHO Chemical Industry Co., LTD, Tradename) | |
| Xanthan gum | 0.02 part |
| Water | 64.48 parts |

The above materials are uniformly mixed, and then, wet pulverized to make a flowable.

Formulation Example 4

Dry Flowable

| | |
|---|---|
| Compound of the present invention No. 1 | 75 parts |
| HITENOL NE-15 | 5 parts |
| (an anionic surfactant: available from DAI-ICHI KOGYO SEIYAKU CO., LTD., Trade-name) | |
| VANILLEX N | 10 parts |
| (an anionic surfactant: available from Nippon Paper Chemicals Co., Ltd., Trade-name) | |
| CARPREX #80D | 10 parts |

(Synthetic hydrated silicic acid: available from Shionogi & Co., Ltd., Trade-name) The above materials are uniformly mixed and pulverized, and then, a small amount of water is added to the mixture and the resulting mixture is mixed under stirring, granulated by an extrusion granulator, and dried to make a dry flowable.

Formulation Example 5

Granule

| | |
|---|---|
| Compound of the present invention No. 1 | 5 parts |
| Bentonite | 55 parts |
| Talc | 44 parts |

The above materials are uniformly mixed and pulverized, and then, a small amount of water is added to the mixture and the resulting mixture is mixed under stirring, granulated by an extrusion granulator, and dried to make a granule.

In the meantime, the above-mentioned DBSN means sodium dodecyl benzene sulfonate.

Hereinafter, the availability of the compound of the present invention as herbicide will be concretely described based on the following test examples.

Test Example 1

Herbicidal Effect Test in Submerged Condition by Treatment Before Weed-Generation (1)

After alluvial soil was placed in a styrol cup of 1/30000 are, water was poured therein and mixed, and adjusted to a submerged condition of water depth 4 cm. After seeds of *Echinochloa crus-galli*, *Scirpus juncoides* and *Monochoria vaginalis* were sown in the cup, rice seedlings at 2.5th leaf stage were transplanted. On the day when the seeds were sown, the wettable powder of the present invention prepared according to Formulation Example 1 was diluted wt water so as to give a predetermined formulation amount, and the surface of the water was treated with the diluted wettable powder. The plants were grown by putting the cup in a green house at 25 to 30° C., and investigated on herbicidal effect against each weed 3 weeks after treatment with the herbicide according to the following criteria. The results are shown in Table 3.

Criteria

5 Herbicidal rate 90% or more (almost complete death)
4 Herbicidal rate 70% or more and less than 90%
3 Herbicidal rate 40% or more and less than 70%
2 Herbicidal rate 20% or more and less than 40%
1 Herbicidal rate 5% or more and less than 20%
0 Herbicidal rate 5% or less (little effect)

Test Example 2

Herbicidal Effect Test in Submerged Condition by Treatment During Weed-Growth Stage (1)

After alluvial soil was placed in a styrol cup of 1/30000 are, water was poured therein and mixed, and adjusted to a submerged condition of water depth 4 cm. After seeds of *Echinochloa crus-galli*, *Scirpus juncoides* and *Monochoria vaginalis* were sown in the cup, the plants were grown by putting the cup in a green house at 25 to 30° C. When *Echinochloa crus-galli*, *Scirpus Juncoides* and *Monochoria vaginalis* reached 1st to 2nd leaf stage, the wettable powder of the present invention prepared according to Formulation Example 1 was diluted with water so as to give a predetermined formulation amount, and the surface of the water was treated with the diluted wettable powder. The herbicidal effect for each plant was investigated 3 weeks after treatment with the herbicide according to the criteria indicated in Test Example 1. The result are shown in Table 4.

Test Example 3

Herbicidal Effect Test by Soil Treatment

Sterilized diluvial soil was placed in a plastic box having a size of length 21 cm, width 13 cm and depth 7 cm, seeds *Echinochloa crus-galli*, *Digitaria adscendes*, *Setaria viridis*, *Avena fatua*, Black-grass, *Abutilon avicennae*, *Ambrosia ela-* tior, Amaranthus retroflexus, Chenopodium album, Polygonum blumei, Stellaria media, Zea mays (corn), Glycine max (soybean), Oryza sativa (rice), Triticum aestivum (wheat) and Beta vulgaris (beat) were sown interspatially, covered with about 1.5 cm of soil, and then the wettable powder of the present invention prepared according to Formulation Example 1 was diluted with water so as to give a predetermined formulation amount, and the surface of the soil was uniformly treated with the diluted wettable powder by use of a small-sized spray. The herbicidal effect for each plant was investigated 3 weeks after treatment with the herbicide according to the criteria indicated in Test Example 1. The results are shown in Table 5.

Test Example 4

Herbicidal Elect Test by Foliage Treatment

Sterilized diluvial soil was placed in a plastic box having a size of length 21 cm, width 13 an and depth 7 cm, seeds of Echinochloa crus-galli, Digitaria adscendes, Setaria viridis, Avena fatua, Black-grass, Abutilon avicennae, Ambrosia elatior, Amaranthus retroflexus, Chenopodium album, Polygonum blumei, Stellaria media, Zea mays, Glycine max, Oryza sativa, Triticum aestivum and Beta vulgaris were sown interspatially, covered with a 1.5 cm of soil, and then the plants were grown by putting the box in a green house t 25 to 30° C. After growth of 14 days, the wettable powder of the present invention prepared according to Formulation Example 1 was diluted with water so as to give a predetermined formulation amount, and the foliage part was uniformly treated with the diluted wettable powder by use of a small-sized spray. The herbicidal effect for each plant was investigated 3 weeks after treatment with the herbicide according to the criteria indicated in Test Example 1. The results are shown in Table 6.

Test Example 5

Herbicidal Effect Test in Submerged Condition by Treatment Before Weed-Generation (2)

Paddy surface soil was placed in a plastic pot of 1/10000 are, water was poured therein and mixed. After seeds of Scirpus juncoides wee sown, paddy surface soil was added by 2 cm, and submerged with water, and then seeds of Echinochloa crus-galli, Scirpus juncoides, Monochoria vaginalis, Rotala indica and Lindernia pyxidaria were sown together. In addition, rice seedlings at 2.5th leaf stage were transplanted, and fixed to the paddy surface in a state where the roots were exposed on the other side. On the day when the seeds were sown, the wettable powder of the present invention prepared according to Formulation Example 1 was diluted with water so as to give a predetermined formulation amount, and the surface of the water was treated with the diluted wettable powder. The plants were grown by putting the pot in a green house at 25 to 30° C. The herbicidal effort for each plant was investigated 3 weeks after treatment with the herbicide according to the criteria indicated in Test Example 1. The results are shown in Table 7.

Test Example 6

Crop Injury Test on Rice in Water Leakage Condition

A mixed soil of alluvial soil and individual soil was placed in a plastic pot perforated at the bottom of 1/10000 are, water was poured therein and mixed, and then rice seedlings et 2.5th leaf stage were transplanted. War leakage treatment was carried out by placing the pot in a plastic vat, and controlling the amount of water in the vat kept at a condition of 2 cm/day×3 days. The pot was put in a green house at 25 to 30° C., on third day after transplantation, the wettable powder of the present invention prepared according to Formulation Example 1 was diluted water so as to give a predetermined formulation amount, and the surface of the water was treated with the diluted wettable powder. The crop injury on rice was investigated 3 weeks after treatment with the herbicide according to the criteria indicated in Test Example 1 The results are shown in Table 8.

In the symbols in Tables 3 to 8 have the following meanings. A: Echinochloa crus-galli, B: Scirpus juncoides, C: Monochoria vaginalis, D: Digitaria adscendes, E: Setaria viridis, F: Avena fatua, G: Black-grass, H: Abutilon avicennae, I: Ambrosia elatior, J: Amaranthus retroflexus, K: Chenopodium album, L: Polygonum blumei, M: Stellaria media, N: Rotala Indica, O: Lindernia pyxidaria, a: transplanted rice (Oryza sativa), b: corn (Zea mays), c: soybean (Glycine max), d: direct sown rice, e: Triticum aestivum (wheat), f: Beta vulgaris (beet), g: rice transplanted at a depth of 0 cm.

TABLE 3

| Compound No. | Application Dosage (g/a) | A | B | C | a |
|---|---|---|---|---|---|
| 1 | 0.64 | 5 | 5 | 5 | 0 |
| 2 | 0.64 | 4 | 5 | 5 | 0 |
| 3 | 0.64 | 5 | 5 | 5 | 0 |
| 5 | 0.64 | 5 | 5 | 5 | 3 |
| 6 | 0.64 | 5 | 5 | 5 | 3 |
| 7 | 0.64 | 5 | 5 | 5 | 3 |
| 8 | 0.64 | 3 | 4 | 5 | 0 |
| Comparative Compound 1 | 0.64 | 5 | 5 | 5 | 2 |
| Comparative Compound 2 | 0.64 | 5 | 5 | 5 | 4 |

TABLE 4

| Compound No. | Application Dosage (g/a) | A | B | C |
|---|---|---|---|---|
| 1 | 0.64 | 5 | 5 | 5 |
| 2 | 0.64 | 2 | 4 | 4 |
| 3 | 0.64 | 5 | 5 | 5 |
| 4 | 0.64 | 0 | 3 | 3 |
| 5 | 0.64 | 5 | 5 | 5 |
| 6 | 0.64 | 5 | 5 | 5 |
| 7 | 0.64 | 5 | 5 | 5 |
| 8 | 0.64 | 4 | 4 | 4 |
| 9 | 0.64 | 5 | 5 | 5 |
| Comparative Compound 1 | 0.64 | 5 | 5 | 5 |
| Comparative Compound 2 | 0.64 | 5 | 5 | 5 |

TABLE 5

| Compound No. | Application Dosage (g/a) | A | D | E | F | G | H | I | J | K | L | M | b | c | d | e | f |
|---|---|---|---|---|---|---|---|---|---|---|---|---|---|---|---|---|---|
| 1 | 1.6 | 2 | 4 | 1 | 0 | 4 | 4 | 5 | 5 | 5 | 5 | 5 | 5 | 5 | 2 | 5 | 5 |
| 2 | 1.6 | 0 | 0 | 0 |   |   | 0 | 3 | 1 | 4 | 0 | 3 | 0 | 0 | 0 |   | 2 |
| 3 | 1.6 | 2 | 2 | 0 | 0 | 3 | 5 | 5 | 4 | 3 | 5 | 5 | 3 | 1 | 0 | 0 | 4 |
| 4 | 1.6 | 0 | 0 | 0 | 0 | 0 | 0 | 2 | 0 | 1 | 0 | 1 | 0 | 0 | 0 | 0 | 0 |
| 5 | 1.6 | 5 | 5 | 4 |   |   | 4 | 5 | 5 | 5 | 5 | 5 | 5 | 5 | 5 |   | 5 |
| 6 | 1.6 | 4 | 4 | 3 | 0 | 5 | 3 | 5 | 4 | 5 | 5 | 5 | 4 | 3 | 4 | 4 | 4 |
| 7 | 1.6 | 4 | 4 | 4 | 4 | 5 | 4 | 5 | 5 | 5 | 5 | 5 | 4 | 3 | 5 | 5 | 5 |
| 8 | 1.6 | 1 | 3 | 0 | 0 | 3 | 0 | 5 | 5 | 2 | 5 | 4 | 0 | 0 | 2 | 1 | 2 |
| 9 | 1.6 | 4 | 4 | 4 | 3 | 5 | 4 | 5 | 5 | 5 | 5 | 5 | 5 | 5 | 5 | 5 | 5 |

TABLE 6

| Compound No. | Application Dosage (g/a) | A | D | E | F | G | H | I | J | K | L | M | b | c | d | e | f |
|---|---|---|---|---|---|---|---|---|---|---|---|---|---|---|---|---|---|
| 1 | 1.6 | 5 | 5 | 3 | 1 | 4 | 5 | 5 | 5 | 4 | 5 | 5 | 5 | 5 | 0 | 2 | 5 |
| 2 | 1.6 | 3 | 1 | 1 | 0 | 1 | 5 | 4 | 0 | 4 | 0 | 5 | 4 | 4 | 0 | 0 | 4 |
| 3 | 1.6 | 4 | 3 | 2 | 0 |   | 5 | 5 | 0 | 2 | 3 | 5 | 4 | 5 | 0 | 0 | 3 |
| 4 | 1.6 | 0 | 0 | 0 | 0 | 0 | 4 | 3 | 2 | 4 | 3 | 2 | 0 | 3 | 0 | 0 | 1 |
| 5 | 1.6 | 5 | 5 | 4 | 5 | 5 | 5 | 5 | 5 | 5 | 5 | 5 | 5 | 3 | 5 |   | 5 |
| 6 | 1.6 | 5 | 5 | 5 | 3 | 5 | 5 | 5 | 4 | 5 | 5 | 5 | 4 | 4 | 4 | 4 | 5 |
| 7 | 1.6 | 5 | 5 | 4 | 5 | 5 | 5 | 5 | 4 | 5 | 5 | 5 | 5 | 5 | 2 | 5 | 5 |
| 8 | 1.6 | 4 | 3 | 4 | 1 | 0 | 5 | 4 | 4 | 4 | 4 | 4 | 4 | 4 | 1 | 1 | 4 |

TABLE 7

| Compound No. | Application Dosage (g/a) | A | B | C | N | O | a | g |
|---|---|---|---|---|---|---|---|---|
| 1 | 0.3 | 5 | 5 | 5 | 5 | 5 | 0 | 0 |
| Comparative Compound 1 | 0.3 | 5 | 5 | 5 | 5 | 5 | 0 | 3 |
| Comparative Compound 2 | 0.3 | 5 | 5 | 5 | 5 | 5 | 4 | 4 |

TABLE 8

| Compound No. | Application Dosage (g/a) | a |
|---|---|---|
| 1 | 0.15 | 0 |
| Comparative Compound 1 | 0.15 | 3 |
| Comparative Compound 2 | 0.15 | 5 |

Comparative Compounds 1 and 2 are the following compounds disclosed in JP-A-7-118269 (1995).

Comparative Compound 1

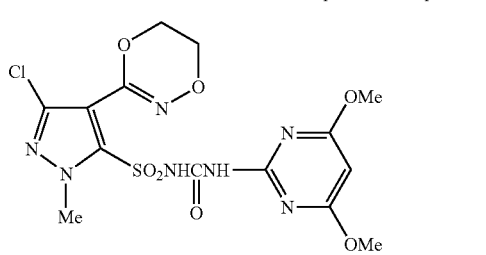

-continued

Comparative Compound 2

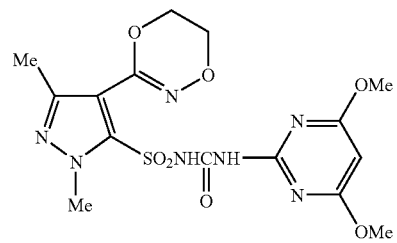

INDUSTRIAL APPLICABILITY

The pyrazole sulfonyl urea compound of the present invention is useful as a selective herbicide for paddy rice and wheat or barley.

The invention claimed is:

1. A pyrazole sulfonylurea compound of formula (1):

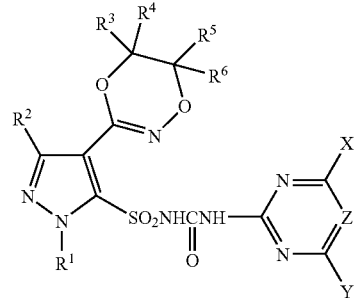

(1)

wherein $R^1$ is $C_{1-3}$alkyl, $C_{1-3}$haloalkyl, $C_{1-3}$alkoxy $C_{1-3}$alkyl, phenyl or pyridyl, $R^2$ is $C_{1-3}$alkyl, $C_{1-3}$haloalkyl, $C_{1-3}$alkoxy or halogen atom, $R^3$, $R^4$, $R^5$ and $R^6$ independently of one another are hydrogen atom, $C_{1-3}$alkyl or $C_{1-3}$haloalkyl, with a proviso that at least one of $R^3$, $R^4$, $R^5$, and $R^6$ is $C_{1-3}$alkyl or $C_{1-3}$haloalkyl, X and Y independently of each other are $C_{1-3}$alkyl, $C_{1-3}$haloalkyl, $C_{1-3}$alkoxy, $C_{1-3}$ haloalkoxy, halogen atom or di($C_{1-3}$alkyl)amino, Z is nitrogen atom or methyne, and a salt thereof.

2. The compound and the salt thereof according to claim 1, wherein $R^1$ is methyl, $R^2$ is methyl or chlorine atom, $R^3$, $R^4$, $R^5$, and $R^6$, independently of one another are hydrogen atom or methyl, with a proviso that at least one of $R^3$, $R^4$, $R^5$ and $R^6$ is methyl, X and Y are methoxy or methyl, Z is nitrogen atom or methyne.

3. The compound and the salt thereof according to claim 2, wherein $R^2$ is methyl.

4. The compound and the salt thereof according to claim 2, wherein $R^2$ is chlorine atom.

5. The compound and the salt thereof according to claim 4, wherein $R^3$ is methyl, $R^4$, $R^5$ and $R^6$ are hydrogen atom.

6. An agrochemical containing at least one of the pyrazole sulfonylurea compound and the salt thereof according to claim 1 as an active component.

7. A herbicide containing at least one of the pyrazole sulfonylurea compound and the salt thereof according to claim 1 as an active component.

* * * * *